(12) United States Patent
Bhatia et al.

(10) Patent No.: US 10,072,257 B2
(45) Date of Patent: Sep. 11, 2018

(54) INVERSE PATTERNING PROCESS FOR THREE-DIMENSIONAL MULTI-COMPARTMENTAL MICRO-ORGANIZATION OF MULTIPLE CELL TYPES

(71) Applicant: Massachusetts Institute of Technology, Cambridge, MA (US)

(72) Inventors: Sangeeta N. Bhatia, Lexington, MA (US); Kelly R. Stevens, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/381,866

(22) PCT Filed: Feb. 28, 2013

(86) PCT No.: PCT/US2013/028345
§ 371 (c)(1),
(2) Date: Aug. 28, 2014

(87) PCT Pub. No.: WO2013/130823
PCT Pub. Date: Sep. 6, 2013

(65) Prior Publication Data
US 2015/0082468 A1 Mar. 19, 2015

Related U.S. Application Data

(60) Provisional application No. 61/619,074, filed on Apr. 2, 2012, provisional application No. 61/604,841, filed on Feb. 29, 2012.

(51) Int. Cl.
| | |
|---|---|
| *C12N 5/00* | (2006.01) |
| *C12N 11/04* | (2006.01) |
| *C12N 5/071* | (2010.01) |
| *A61K 35/12* | (2015.01) |
| *C12N 11/08* | (2006.01) |
| *C12N 11/10* | (2006.01) |
| *G01N 33/50* | (2006.01) |

(52) U.S. Cl.
CPC .............. *C12N 11/04* (2013.01); *A61K 35/12* (2013.01); *C12N 5/0012* (2013.01); *C12N 5/0062* (2013.01); *C12N 5/0671* (2013.01); *C12N 11/08* (2013.01); *C12N 11/10* (2013.01); *G01N 33/5005* (2013.01); *C12N 2533/76* (2013.01); *C12N 2535/10* (2013.01)

(58) Field of Classification Search
CPC ......... C12N 11/04; C12N 11/08; C12N 11/10; C12N 5/0012; C12N 5/0062; C12N 5/0671; C12N 2533/76; C12N 2535/10; A61K 35/12; G01N 33/5005
See application file for complete search history.

(56) References Cited

U.S. PATENT DOCUMENTS

| | | | |
|---|---|---|---|
| 2006/0258000 A1 | 11/2006 | Allen et al. | |
| 2006/0270032 A1 | 11/2006 | Bhatia et al. | |
| 2008/0075750 A1* | 3/2008 | Akins, Jr. | ............... A61K 35/34 424/423 |
| 2009/0018033 A1* | 1/2009 | Morgan | ............... C12N 5/0012 506/26 |

FOREIGN PATENT DOCUMENTS

WO 2004/046337 A2 6/2004

OTHER PUBLICATIONS

Choi et al. "Patterning and transferring hydrogel-encapsulated bacterial cells for quantitative analysis of synthetically engineered genetic circuits." Biomaterials. Jan. 2012;33(2):624-33. doi: 10.1016/j.biomaterials.2011.09.069. Epub Oct. 19, 2011.*
Qiu et al. "Generation of Uniformly Sized Alginate Microparticles for Cell Encapsulation by Using a Soft-Lithography Approach." Advanced Materials 19.12 (2007): 1603-1607.*
Nahmias, Y., et al., "Integration of technologies for hepatic tissue engineering," Adv Biochem Eng Biotechnol., vol. 103:309-329 (2007).
Nahmias, Y., et al., "Laser-guided direct writing for three-dimensional tissue engineering," Biotechnol Bioeng., vol. 92(2):129-136 (2005).
Nelson, C. M., et al., "Tissue geometry determines sites of mammary branching morphogenesis in organotypic cultures," Science, vol. 314(5797): 298-300 (2006).
Parenteau, N. L., "Commercial development of cell-based therapeutics: strategic considerations along the drug to tissue spectrum," Regen Med., vol. 4(4): 601-611 (2009).
Peshwa, M. V., et al., "Mechanisms of formation and ultrastructural evaluation of hepatocyte spheroids," In Vitro Cell Dev Biol Anim., vol. 32(4): 197-203 (1996).
Raghavan, S., et al., "Geometrically controlled endothelial tubulogenesis in micropatterned gels," Tissue Eng Part A., vol. 16(7):2255-2263 (2010).

(Continued)

*Primary Examiner* — Titilayo Moloye
(74) *Attorney, Agent, or Firm* — Nelson Mullins Riley & Scarborough LLP; Amy E. Mandragouras, Esq.; Ariana D. Harris

(57) ABSTRACT

The invention features an "inverse patterning" or "Intaglio-Void/Embed-Relief Topographic (In VERT) molding" manufacturing process for generating high-resolution three-dimensional (3D) multi-cellular microstructures in distinct cellular compartments of a single hydrogel. The platform has general utility in the development of engineered tissues for human therapies, drug testing, and disease models. Additionally, the platform can serve as a model system for studying 3D cell-cell interactions in fields as diverse as stem cell biology to the development of cancer therapeutics.

18 Claims, 16 Drawing Sheets

(56) References Cited

OTHER PUBLICATIONS

Rago, A. P., et al., "Encapsulated Arrays of Self-Assembled Microtissues: An Alternative to Spherical Microcapsules," Tissue Eng Part A 15, 387-395 (2009).
Schwartz, R.E., et al., "Modeling hepatitis C virus infection using human induced pluripotent stem cells," Proc Natl Acad Sci USA, vol. 109(7):2544-2548 (2012).
Seglen, P. O., "Preparation of isolated rat liver cells," Methods Cell Biol., vol. 13: 29-83 (1976).
Si-Tayeb, K. et al., "Highly efficient generation of human hepatocyte-like cells from induced pluripotent stem cells," Hepatology, vol. 51(1): 297-305 (2010).
Stevens KR, et al., "InVERT molding for scalable control of tissue microarchitecture," Nat Commun., vol. 4 (1847) doi:10.1038/ncomms2853 (2013).
Stevens, K. R et al., "Physiological function and transplantation of scaffold-free and vascularized human cardiac muscle tissue," Proc Natl Acad Sci USA., vol. 106(39): 16568-16573 (2009).
Takahashi K. et al., "Induction of pluripotent stem cells from mouse embryonic and adult fibroblast cultures by defined factors," Cell, vol. 126 (4): 663-676 (2006).
Tan, W. et al., "Layer-by-layer microfluidics for biomimetic three-dimensional structures," Biomaterials, vol. 25 (7-8):1355-1364, (2004).
Tekin, H., et al., "Responsive micromolds for sequential patterning of hydrogel microstructures," J Am Chem Soc., vol. 133(33): 12944-12947 (2011).
Tsang, L. V et al., "Three-dimensional tissue fabrication," Advanced Drug Delivery Reviews, Elsevier BV, Amsterdam, NL, vol. 56(11):1635-1647 (2004).
Tsang, L.V. et al., "Fabrication of 3D hepatic tissues by additive photopatterning of cellular hydrogels," FASEB J., vol. 21(3): 790-801 (2007).
Tsuda, Y. et al., "Cellular control of tissue architectures using a three-dimensional tissue fabrication technique," Biomaterials, vol. 28(33): 4939-4946 (2007).
Underhill, G. H. et al., "Assessment of hepatocellular function within PEG hydrogels," Biomaterials, vol. 28(2):256-270 (2007).
Ungrin, M. D., et al., :Reproducible, Ultra High-Throughput Formation of Multicellular Organization from Single Cell Suspension-Derived Human Embryonic Stem Cell Aggregates, PLoS One vol. 3 (2):e1565(2008).
Williams, C. M. et al., "Autocrine-Controlled Formation and Function of Tissue-Like Aggregates by Primary Hepatocytes in Micropatterned Hydrogel Arrays," Tissue Eng Part A vol. 17 (7-8), 1055-1068 (2011).
Wong, S. F., et al., "Concave microwell based size-controllable hepatosphere as a three-dimensional liver tissue model," Biomaterials, vol. 32(32):8087-8096 (2011).
Wylie, R. G. et al., "Spatially controlled simultaneous patterning of multiple growth factors in three-dimensional hydrogels," Nat Mater., vol. 10 (10): 799-806 (2011).
Zhang, S. C. et al., "In vitro differentiation of transplantable neural precursors from human embryonic stem cells," Nat Biotechnol., vol. 19(12): 1129-1133(2001).
Abu-Absi, S. F. et al., "Structural polarity and functional bile canaliculi in rat hepatocyte spheroids," Exp Cell Res., vol. 274(1):56-67 (2002.
Aird, W. C., "Endothelium in health and disease," Pharmacol Rep. vol. 60 (1):139-143 (2008).
Akselrod, G. M. et al., "Laser-guided assembly of heterotypic three-dimensional living cell microarrays," Biophys J., vol. 91 (1): 3465-3473 (2006).
Albrecht, D. R., et al."Probing the role of multicellular organization in three-dimensional microenvironments," Nat Methods, vol. 3(5): 369-375 (2006).
Antonchuk, J. et al., "AggreWell 400 and AggreWell 800 Provide a Unique Platform for Generation of Size-Controlled Aggregates Including Human Embryoid Bodies," STEMCell Technologies, Poster Presentation, 1 page (2010).
Atala, A., "Engineering organs," Curr Opin Biotechnol., vol. 20(5):575-592 (2009).
Barron, J. A, et al., "Biological laser printing: a novel technique for creating heterogeneous 3-dimensional cell patterns," Biomed Microdevices, vol. 6 (2):139-147 (2004).
Berry, MN et al., "High-yield preparation of isolated rat liver parenchymal cells: a biochemical and fine structural study," Cell Biol., vol. 43(3):506-520 (1969).
Bhatia, S. N., et al."Effect of cell-cell interactions in preservation of cellular phenotype: cocultivation of hepatocytes and nonparenchymal cells," FASEB J., vol. 13 (14):1883-1900 (1999).
Brophy, C. M. et al."Rat hepatocyte spheroids formed by rocked technique maintain differentiated hepatocyte gene expression and function," Hepatology vol. 49(2):578-586 (2009).
Chen, A. A., et al., "Humanized mice with ectopic artificial liver tissues," Proc Natl Acad Sci USA, vol. 108(29):11842-11847 (2011).
Cleaver, O.et al., "Endothelial signaling during development," Nat Med, vol. 9(6):661-668 (2003).
Culver, J. C., et al., "Three-dimensional biomimetic patterning in hydrogels to guide cellular organization," Adv Mater, vol. 24(17):2344-2348 (2012).
DeForest, C. A., et al.,"Cytocompatible click-based hydrogels with dynamically tunable properties through orthogonal photoconjugation and photocleavage reactions," Nat Chem., vol. 3(12):925-931 (2011).
Ding, B. S. et al., "Endothelial-derived angiocrine signals induce and sustain regenerative lung alveolarization," Cell, vol. 147(3):539-553 (2011).
Ding, B. S. et al., "Inductive angiocrine signals from sinusoidal endothelium are required for liver regeneration," Nature, vol. 468(7321):310-315 (2010).
Du, Y, et al., "Directed assembly of cell-laden microgels for fabrication of 3D tissue constructs," Proc Natl Acad Sci USA, vol. 105(28):9522-9527 (2008).
Dunn, J. C., et al., "Long-term in vitro function of adult hepatocytes in a collagen sandwich configuration," Biotechnol Prog., vol. 7(3):237-245 (1991).
Ennett, A. B. et al., "Tissue engineering strategies for in vivo neovascularisation," Expert Opin Biol Ther., vol. 2(8):805-818 (2002).
Franses, J. W., et al., "Stromal endothelial cells directly influence cancer progression," Sci Transl Med., vol. 3(66):66ra5, 18 pages (2011).
Glicklis, R., et al., "Hepatocyte behavior within three-dimensional porous alginate scaffolds," Biotechnol Bioeng., vol. 67(3), 344-353 (2000).
Hamada, H., "In search of Turing in vivo: understanding Nodal and Lefty behavior," Dev Cell, vol. 22(5): 911-912 (2012).
He, J. Q. et al., "Human embryonic stem cells develop into multiple types of cardiac myocytes: action potential characterization," Circ Res., vol. 93(1): 32-39 (2003).
Hui, E. et al., "Micromechanical control of cell-cell interactions," Proc Natl Acad Sci USA, vol. 104(14):5722-5726 (2007).
Inman, J. L. et al., "Apical polarity in three-dimensional culture systems: where to now?," J Biol., vol. 9(1): 2 (2010).
International Preliminary Report on Patentability, PCT/US2013/028345, dated Sep. 2, 2014, 6 pages.
International Search Report and Written Opinion, PCT/US2013/028345, dated May 24, 2013, 9 pages.
Jakab, K, et al., "Engineering biological structures of prescribed shape using self-assembling multicellular systems," Proc Natl Acad Sci USA, vol. 101(9):2864-2869 (2004).
Jakab, K., et al., "Tissue engineering by self-assembly and bio-printing of living cells," Biofabrication, vol. 2(2): 022001(2010).
Khetani, S. R., et al., "Microscale culture of human liver cells for drug development," Nat Biotechnol., vol. 26(1):120-126 (2008).
Khetani, SR et al., "T-cadherin modulates hepatocyte functions in vitro," FASEB J vol. 22(11):3768-3775 (2008).
Khetani, SR. et al., "Exploring interactions between rat hepatocytes and nonparenchymal cells using gene expression profiling," Hepatology, vol. 40(3):545-554 (2004).

(56) References Cited

OTHER PUBLICATIONS

Kloxin, A. M., et al. "Photodegradable hydrogels for dynamic tuning of physical and chemical properties," Science, vol. 324(5293): 59-63 (2009).
Lammert, E., et al., "Induction of pancreatic differentiation by signals from blood vessels," Science, vol. 294(5542):564-567 (2001).
Lammert, E., et al., "Role of endothelial cells in early pancreas and liver development," Mech Dev., vol. 120(1): 59-64 (2003).
Landry, J., et al., "Spheroidal aggregate culture of rat liver cells: histotypic reorganization, biomatrix deposition, and maintenance of functional activities," J Cell Biol, vol. 101(3): 914-923 (1985).
Lee, H. et al., "Local Delivery of Basic Fibroblast Growth Factor Increases Both Angiogenesis and Engradtment of Hepatocytes in Tissue-Engineered Polymer Devices," Transplantation, vol. 73:1589-1593 (2002).
Levenberg, S. et al., "Engineering vascularized skeletal muscle tissue," Nat Biotechnol., vol. 23(7): 879-884 (2005).
Lu, H. F. et al., "Three-dimensional co-culture of rat hepatocyte spheroids and NIH/3T3 fibroblasts enhances nepatocyte functional maintenance," Acta Biomater., vol. 1(4):399-410 (2005).
MacNeil, S., "Progress and opportunities for tissue-engineered skin," Nature vol. 445(7130):874-880 (2007).
Mailleux, A. A., et al., "Lumen formation during mammary epithelial morphogenesis: insights from in vitro and in vivo models," Cell Cycle, vol. 7 (1) :57-62 (2008).
March, S., et al., "Microenvironmental regulation of the sinusoidal endothelial cell phenotype in vitro," Hepatology, vol. 50(3):920-928 (2009).
Matsumoto, K., "Liver organogenesis promoted by endothelial cells prior to vascular function," Science, vol. 294(5542):559-563 (2001).
Mikos, A. G., et al., "Engineering Complex Tissues," Tissue Eng vol. 12 (12): 3307-3339(2006).
Miller, J. S., et al. "Rapid casting of patterned vascular networks for perfusable engineered three-dimensional tissues," Nat Mater., vol. 11(9): 768-774 (2012).
Mironov, V. et al., "Organ printing: tissue spheroids as building blocks," Biomaterials, vol. 30(12):2164-2174 (2009).
Mironov, V., et al., "Organ printing: computer-aided jet-based 3D tissue engineering.," Trends Biotechnol., vol. 21(4):157-161 (2003).
Moscona, A., "Rotation-mediated histogenetic aggregation of dissociated cells. A quantifiable approach to cell interactions in vitro," Exp Cell Res., vol. 22:455-475 (1961).
Muller, P., et al., "Differential diffusivity of Nodal and Lefty underlies a reaction-diffusion patterning system," Science, vol. 336(6082): 721-724(2012).
Muller, P., et al., "Extracellular movement of signaling molecules," Dev Cell., vol. 21(1): 145-158 (2011).
Sakai, Y., et al., "A New Bioartificial Liver Using Porcine Hepatocyte Spheroids in High-Cell-Density Suspension Perfusion Culture: In Vitro Performance in Synthesized Culture Medium and in 100% Human Plasma," Cell Transplant, vol. 8(5):531-541 (1999).

\* cited by examiner

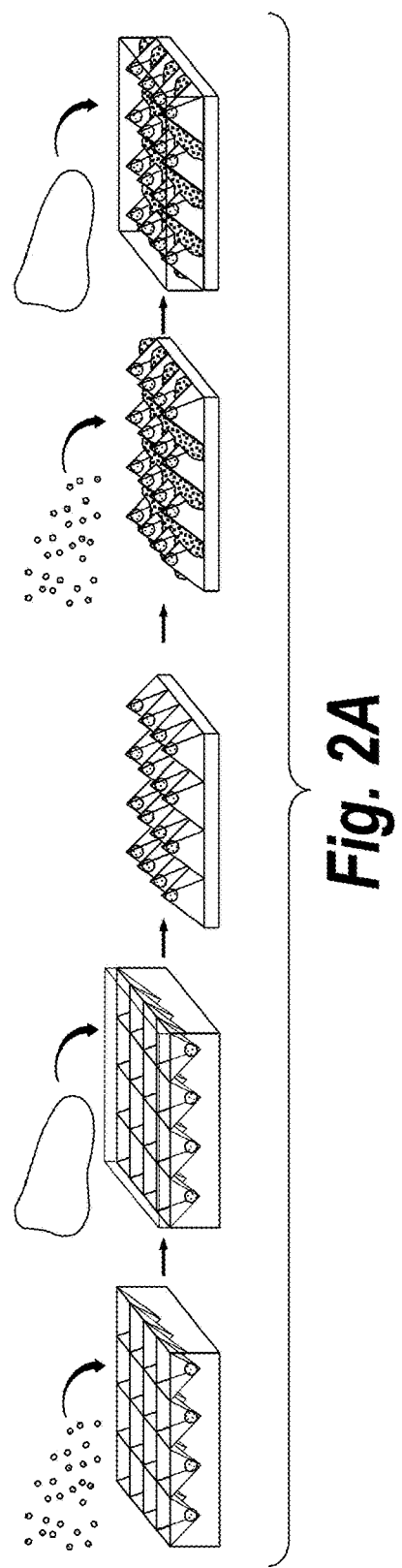

INVERSE PATTERNING PROCESS FOR THREE-DIMENSIONAL MULTI-COMPARTMENTAL MICRO-ORGANIZATION OF MULTIPLE CELL TYPES

CROSS-REFERENCE TO RELATED APPLICATIONS

This application is a 35 U.S.C. 371 national stage filing of International Application PCT/US2013/028345, filed 28 Feb. 2013, which claims priority to U.S. Patent Application No. 61/604,841, filed 29 Feb. 2012 and U.S. Patent Application No. 61/619,074, filed 2 Apr. 2012. The contents of the aforementioned are hereby incorporated by reference.

STATEMENT OF FEDERALLY SPONSORED RESEARCH

This invention was made with government support under grant nos. EB008396 and DK56966 awarded by the National Institutes of Health (NIH). The government has certain rights in the invention.

BACKGROUND

Cells sense and respond to cues in local their environment, such as signals produced by neighboring cells as well as the chemistry and mechanics of the surrounding matrix. The spatial organization of cells within tissues, or tissue "architecture", defines the cell-cell contacts and paracrine signaling gradients thought to ultimately drive tissue function. Reconstruction of complex tissues for applications in regenerative medicine requires the ability to build three-dimensional (3D) tissues with multi-cell type environment.

Recent studies have demonstrated that three-dimensional (3D) micro-scale organization of a single cell type dictates cell behavior and function in vitro (Albrecht, D. R., et al. *Nat Methods* 3, 369-375 (2006); Nelson, C. M., et al. *Science* 314, 298-300 (2006); and Ungrin, M. D., et al. *PLoS One* 3, e1565 (2008)). However, the 'top-down' dielectrophoresis and molding techniques used in these studies enabled micro-scale organization of only a single cell type in a single engineered tissue layer. Scaling these techniques to enable the organization of multiple cell types across distinct compartments would require separate fabrication of multiple layers followed by tedious manual alignment and lamination. Such assembly prevents patterning of multiple cellular compartments in a single Z plane.

To address this issue, 'bottom-up' technologies such as laser and inkjet-based bioprinting have been used to attain multi-cellular 3D spatial organization in a single Z-plane. However, trade-offs between printing time, resolution, and scale-up as well as between cell density and damage have precluded the use of these methods for widely using these methods to study the relationship between tissue architecture and function. A major unmet challenge is to develop robust methods for spatially patterning 3D cell cultures and to then use these methods to understand how complex multi-level tissue structure controls physiologic function in vitro and after implantation.

SUMMARY OF THE INVENTION

The present invention features an "inverse patterning" methodology referred to as or "Intaglio-Void/Embed-Relief Topographic (InVERT) molding." The inverse patterning" or "InVERT" platform described herein offers numerous advantages and improvements over existing methods for patterning cells in 3D. First, the versatility of previous technologies such as laser printing, dielectrophoresis, photo-patterning, and cell "bioprinting" (see e.g., Albrecht, D. R, et al. *Nat Methods* 3, 369-375, (2006); Nelson, C. M., et al. *Science* 314, 298-300, (2006); Ungrin, M. D., et al. *PLoS One* 3, (2008); Du, Y, et al. *Proc Natl Acad Sci USA* 105, 9522-9527 (2008); Tan, W. & Desai, T. *Biomaterials* 25, 1355-1364, (2004); Liu Tsang, V. et al. *FASEB J* 21, 790-801, (2007); Akselrod, G. M. et al. *Biophys J* 91, 3465-3473, (2006); Mironov, V., et al. *Trends Biotechno/*21, 157-161, (2003); Barron, J. A, et al. *Biomed Microdevices* 6, 139-147 (2004); Jakab, K, et al. *Proc Natl Acad Sci USA* 101,2864-2869, (2004); Tsuda, Y. et al. *Biomaterials* 28, 4939-4946, (2007); Mironov, V. et al. *Biomaterials* 30,2164-2174, (2009); and Nahmias, Y., et al. *Biotechnol Bioeng* 92, 129-136, (2005)) is limited by the technical parameters of the system such as poor printer resolution, printing time, and specific material conductivities.

Second, to build tissues containing multiple distinctly patterned cell types, many of the existing technologies first require patterning of each cell type in a separate hydrogel layer separately followed by tedious manual alignment and merger of layers. Third, these technologies typically rely on external physical forces such as electricity, UV light, and mechanical perturbation that have the potential to damage living cells. Finally, most patterning technologies use "immediate trapping" of cells in a biomaterial without prior cell-cell pre-aggregation, which results in low cellular density in microstructures and interferes with the formation of intercellular junctions that are critical for normal physiologic function in many tissues. In short, previous "top-down" engineering approaches have not achieved robust micro-scale, multi-cellular, and multi-compartmental patterning. Alternatively, "bottom-up" approaches simply have not yet achieved the efficiency and scalability required for large-scale and high-throughput construction of engineered tissues and model systems.

The inverse patterning process described here yields high-resolution multi-cellular microstructures that can be patterned in distinct compartments in 3D hydrogels. This process is highly versatile. It has been shown that the technology is compatible with material systems and patterning substrates found routinely in basic biological laboratories (e.g., agarose or fibrin) as well as highly-tunable and customizable materials (e.g., polyethylene glycol) found in specialized engineering and chemistry laboratories. This process can also be used to pattern cells that have been pre-incubated to enable the formation of intercellular junctions in a given compartment or immediate trapping to produce rapid cell patterns. This process is based on cellular sedimentation and therefore invokes minimal damage to cells. Finally, this process achieves multi-compartmental patterning without the need for manual alignment of cell layers and can produce scaled tissues of clinically relevant sizes.

This process improves on previous technologies in which cells are micro-molded in patterning substrates. In particular, the inverse patterning process of the instant invention features several sequential cooperative steps, including the following: (1) cell patterns are encapsulated in a biomaterial and de-molded from the patterning substrate, (2) inversion of the hydrogel to expose another patterning substrate, and, most importantly, (3) layering of a second micro-molded cell population in a second hydrogel to ultimately form a single gel unit.

The methodology of the instant invention is particularly suitable for the generation of biological tissues (tissue engineering) in which appropriate physiological parameters are controlled such that desired tissue function is achieved. In particular, parenchymal cell function can be controlled in the engineered tissues of the invention supporting the function of complex tissues such as liver, kidney and heart. Tissue function is ultimately driven by cell-cell contacts and paracrine signaling gradients, which are in turn defined by the spatial organization of cells, or 'tissue architecture'. Reconstruction of complex tissues therefore requires a detailed understanding of how multi-cellular and multi-compartmental tissue architecture dictates cell function.

To date, engineered tissues that have been successfully translated to the clinic (e.g., bladder and skin, see Atala, A. *Curr Opin Biotechnol* 20, 575-592 (2009) and Parenteau, N. L. *Regen Med* 4, 601-611 (2009)) contain few cell types and have simple organizational structure. In contrast, construction of more complex tissues (e.g., liver, kidney, and heart) that contain multiple functionally and morphologically distinct but interacting compartments has seen little success. This is due in large part to inadequate parenchymal function of these engineered tissues. The present invention addresses such problems and enables the generation of engineered tissues that can ultimately find use in clinical settings.

DETAILED DESCRIPTION

Complex tissues such as liver, kidney, and heart contain numerous cell types that are organized across morphologically and functionally distinct compartments. Construction and physiological optimization of such tissues, i.e., engineered tissues, in the past has been precluded by limitations in tissue fabrication techniques, which do not enable versatile microscale organization of multiple cell types in tissues of size adequate for physiologic studies and tissue therapies. The instant invention features an inverse patterning platform methodology, referred to as "Intaglio-Void Embedded-Relief Topographic" or "InVERT" molding method for microscale organization of many cell types, including induced pluripotent stem cell (iPS)-derived progeny, within a variety of synthetic and natural extracellular matrices and across tissues of sizes appropriate for in vitro, pre-clinical, and clinical biologic studies. This methodology provides for versatile and scalable 3D micro-organization of multiple cell types across separate compartments in hydrogels. The instant inventors have demonstrates the versatility and scalability of the methodology in the formation of thousands of hepatic cellular aggregates of precisely controlled size and cellular composition encased within a distinct endothelial cell lattice. It is demonstrated that compartmental placement of the endothelial lattice as well as micro-structural optimization of hepatic aggregate size and cellular composition enables modulation of hepatic tissue functions. In particular, it is demonstrated that compartmental placement of non-parenchymal cells relative to primary or iPS-derived hepatocytes and hepatic compartment microstructure and cellular composition modulate hepatic functions. Cellular configurations found to be optimal through in vitro experimentation, i.e., those that sustain physiologic in vitro function, also result in superior tissue survival and physiologic function after transplantation into animals, e.g., mice for significant lengths of time after implantation (e.g., at least 4 weeks), demonstrating the importance of the optimization of architecture prior to implantation. This platform can be used to study multicellular interactions and engineered tissue structure in systems broadly ranging from stem cell and cancer biology to tissue engineering.

Figure 1A:
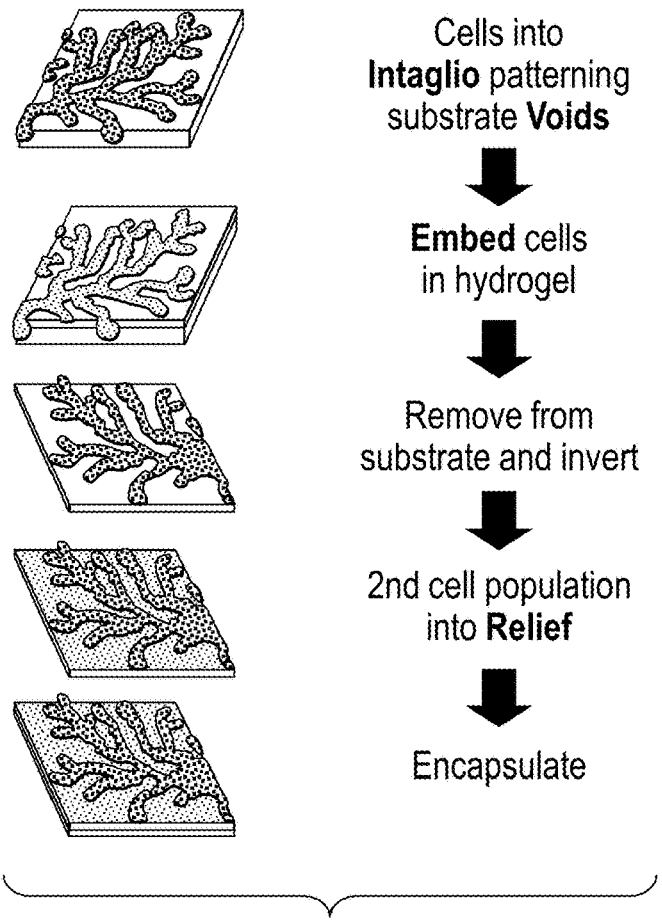
FIG. 1. Fabrication method and versatility for InVERT molding platform. (a) Process flow diagram for creation of 3D hydrogels containing multiple cell types patterned in distinct compartments by intaglio-relief or InVERT molding. (b) Substrate-based molding can produce hydrogels of 1.5 cm diameter (inset) as well as of clinically-relevant sizes (14 cm diameter). Here, size and spacing (800 µm) of cellular clusters was increased to enable visualization of cellular patterns by naked eye after hematoxylin staining. (c) InVERT molding produces multi-cellular and multi-compartmental patterning and is compatible with various substrates and material systems. Here, endothelial cells (green; calcein-AM) and fibroblasts (red; calcein red-orange-AM) are patterned in agarose using a substrate molded using a corner cube bike reflector (middle), or in fibrin gel using a custom-fabricated branching pattern substrate (top; scale bar 500 µm unless otherwise denoted). Green and red cells in all images are labeled using calcein dyes, which are retained only by living cells with intact plasma membranes. (d) InVERT molding is compatible with many cell types. Mouse C2C12 skeletal myoblasts, mouse J2-3T3 fibroblasts, human ovarian carcinoma cells (OVCAR-8), stromal mouse embryonic fibroblasts (10T1/2), human cervical cancer cells (HeLa), normal human dermal fibroblasts (NHDF), and human iPS-hepatocyte-like cells with liver endothelial cells (TMNK1; LEC) were labeled with calcein dyes and patterned in fibrin gel using InVERT molding (scale bars 300 µm).

Exemplary aspects of the invention feature processes by which to encapsulate multiple cell types with distinct organization into a 3D hydrogel (FIG. 1a). In an exemplary embodiment, cells are first isolated in the micro-scale features of polydimethyl siloxane (PDMS) cell-capture substrate either in media or in a pre-polymer material. Cells patterned in media are incubated overnight to allow formation of cell-cell junctions, e.g., cadherin and adhesion junctions, and then encapsulated in a biomaterial, a step referred to herein as pre-incubation. Cells in pre-polymer are trapped immediately after patterning by triggering material polymerization, a step referred to herein as immediate trapping. 3D materials containing cell patterns are then removed from the patterning substrate and inverted, resulting in the exposure of an 'inverse pattern' of micro-scale recesses formed by molding of the material to the PDMS substrate. A second cell population is then loaded within a prepolymer solution to produce an inverse pattern, and polymerization is triggered to trap and encapsulate cells. This process results in the formation of a single 3D biomaterial gel system containing two different micropatterned cellular compartments.

Figure 1B:
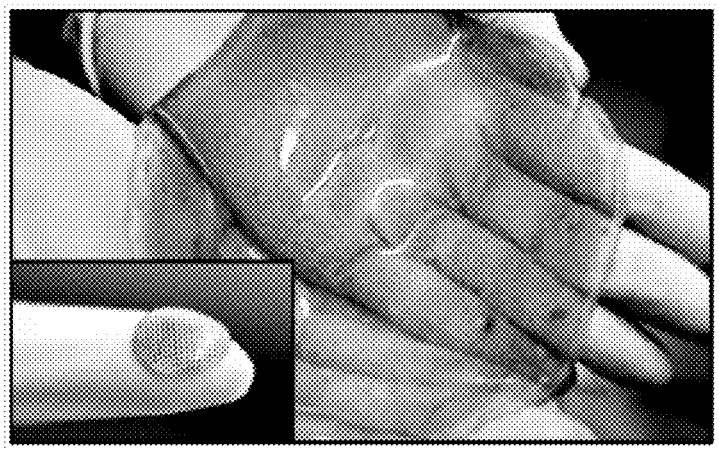
Figure 1C:
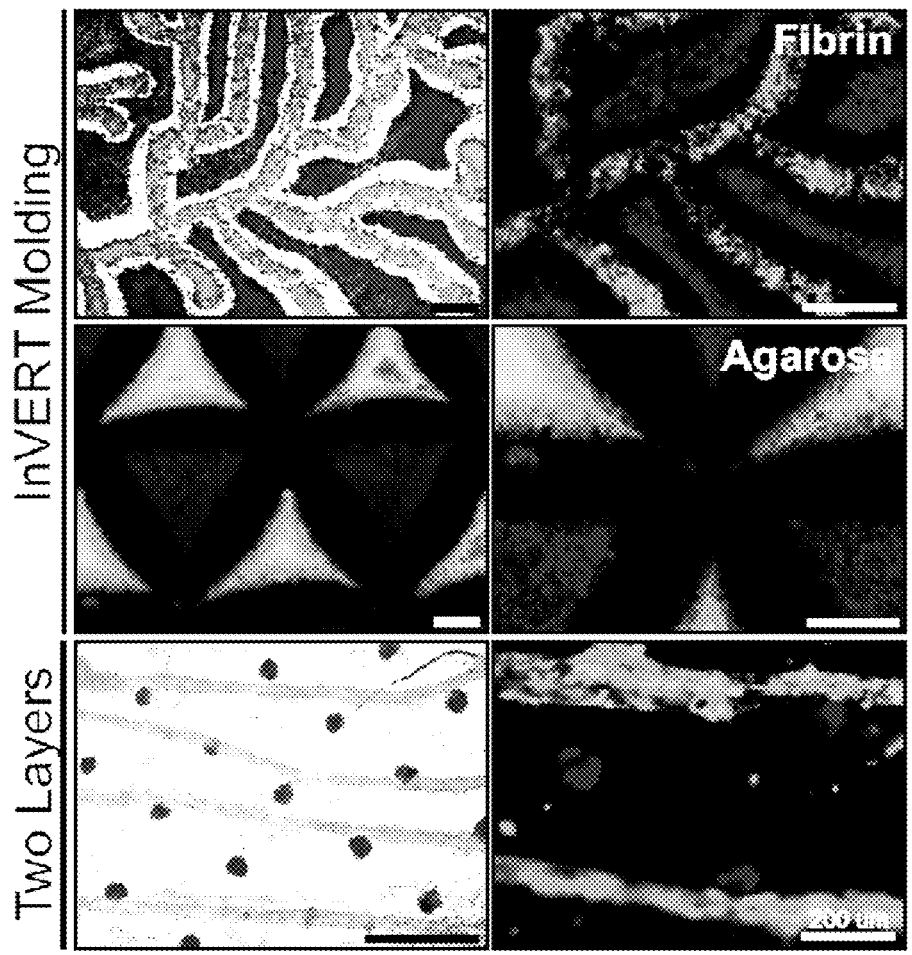
Figure 6:
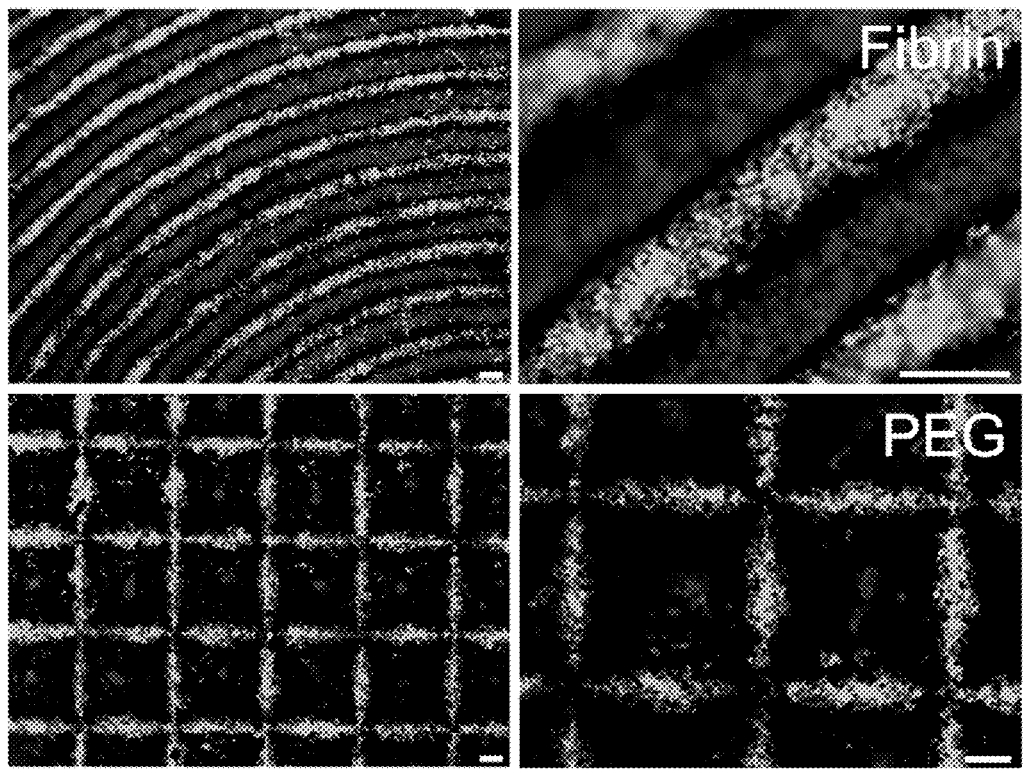
FIG. 6. InVERT molding produces multi-compartmental cellular patterning and is compatible with various topographic patterning substrates and material systems. Top, endothelial cells (green) and fibroblasts (red) are patterned in fibrin. Bottom, hepatocytes (red) and endothelial cells (green) are patterned in polyethylene glycol (PEG). Scale bar 200 μm for all images.

This process can produce a variety of multi-cellular patterns in multiple material systems (FIG. 1c). The instant examples feature encapsulating cells in agarose, fibrin, and polyethylene hydrogels using this approach (FIGS. 1c and 6). This process is readily scalable. Constructs, e.g., hydrogels of up to 15 cm in diameter have been constructed with clear potential for generating constructs e.g., hydrogels of significantly increased sizes (FIG. 1b).

In a preferred aspect, the invention features methods for making three-dimensional, multiple cell type tissue constructs The methodology is referred herein as "inverse patterning", or more specifically, Intaglio-Void/Embed-Relief Topographic (InVERT) molding". In exemplary embodiments, the methods feature (a) introducing a first population of cells into features of a patterned (e.g., micropatterned) cell capture substrate, (b) optionally, incubating said cells under conditions sufficient for formation of cell-cell junctions between cells in said features;

(c) encapsulating said first cell population in a first polymerizable biomaterial;

(d) removing and inverting said encapsulated first cell population;

(e) contacting said inverted, encapsulated first cell population with a second population of cells in a second polymerizable biomaterial; and (f) encapsulating said second population in said second polymerizable biomaterial, in order that the three-dimensional, multiple cell type tissue construct is made.

In exemplary embodiments, the patterned cell capture substrate consists of polydimethyl siloxane (PDMS) comprising micro-scale features. As use herein, "microscale features" are features (e.g., one or more features of a three-dimensional object or structure) having at least one dimension measured on a micrometer scale, i.e., at least 1 and up to 1000 μm. In exemplary embodiments, microscale features are arranges in a repeating pattern, which is termed herein as a "micropattern." In essence, a "micropattern" is one having repeating features on the microscale. For example, a micropattern can include repeating circles or spheres having a diameter on the micrometer scale, or a micropattern can include repeating lines having line widths on the micrometer scale, or a micropattern can include repeating units, e.g., squares, triangles, diabonds, rhomboids, or other two- or three-dimensional geometric shapes, said shapes having at least one feature, e.g., height, width, length, etc. on the micrometer scale. Other micropatterns are contemplated for use in the methods and/or constructs of the invention and can include free-form shapes and/or geometries, etc. Micropatterns are routinely generated using art-recognized micro-patterning techniques including, but not limited to lithography, stenciling, etching, and the like.

In exemplary embodiments, a population of cells, e.g., a first population of cells, is introduced into one or more features of the patterned (e.g., micropatterned) cell capture substrate in solution, e.g., in media or in a pre-polymer solution.

In some embodiments, the cells, e.g., the first population of cells, is incubated in the features of the patterned (e.g., micropatterned) cell culture substrate for a period of time sufficient for cells within the population to establish cell-cell contact and/or cell-cell junctions. In exemplary embodiments, the cells, e.g., the first population of cells, is incubated in the features of the patterned (e.g., micropatterned) for a period of about 6 to about 24 hours, e.g., about 8 to about 16 hours, e.g., about 12 hours, to permit formation of cell-cell junctions between said cells.

In preferred embodiments, the cells are introduced into the features of the patterned (e.g., micropatterned) cell culture substrate in a solution which is a polymerizable biomaterial. As used herein the term "polymerizable biomaterial" is a material which exists initially as a solution of pre-polymer molecules or chains and is biocompatible, which as further capable of being induced to polymerize, e.g., via light (e.g., UV light) or chemical means (e.g., via an polymerization initiator), preferably in a manner such that the material remains biocompatible throughout the polymerization process. In exemplary embodiments, the polymerizable biomaterial is a hydrogel material. Preferred hydrogel materials of the invention include, but are not limited to agarose, fibrin, or polyethylene hydrogel. e.g., photopolymerized polyethylene glycol (PEG) hydrogel. In some embodiments, the polymerizable biomaterial is biodegradable.

Following polymerization of a population of cells, e.g., a first population of cells, such cell population (in polymerized biomaterial (e.g., hydrogel) is removed from the patterned (e.g., micropatterned) substrate and the material (including cells encapsulated therein) is inverted. Subsequently, said inverted, encapsulated cell population (e.g., first cell population) is contacted with a second population of cells in a second polymerizable biomaterial (e.g., hydrogel); and finally said second population is encapsulated in said second polymerizable biomaterial e.g., hydrogel), in order that a three-dimensional, multiple cell type tissue construct is made.

In exemplary embodiments, the cells of the first population are different from those of the second population and preferable, said cell populations are known or suspected to have a detectable influence on each other (or at least a detectable influence of one on the other cell population.) For example, one of the cell populations (e.g., the first or second cell population) can include parenchymal cells the other cell population (e.g., the second or first cell population) can include non-parenchymal cells. In exemplary embodiments, one or more cell populations is a pure cell population, i.e., comprising cells of a single cell type. Alternatively, one or more cell populations can be a mixed population, i.e., comprising cells of at least two and possible more cell types. In certain embodiments, the first and/or second cell population comprises a combination of parenchymal and non-parenchymal cells. In preferred aspects, one or more cell types and/or cell populations is human in mature, .i.e., isolated or derived from human biological sample(s). Exemplary cells of interest are human parenchymal cells.

In order to facilitate, promote, enhance, or otherwise modulate (including down-modulate) cellular behavior of one or more cells or cell types, polymerizable biomaterials of the invention, e.g. hydrogels, can be derivatized with one or more cell-adhesive peptides, or can include one or more soluble factors supporting cell function, e.g., growth and/or differentiation.

Preferably, cells are included in the various compartments of the constructs of the invention in a concentration such the cells of the population can influence other cells in the construct (e.g., can exert homotypic and/or heterotypic influences on other cells in the construct), either within or across cell types and/or populations. Optionally, cells are included in the various compartments of the constructs of the invention in a concentration such one or more activities or phenotypes of the cells is detectable via routine research means. In exemplary embodiments, cells in one or more compartments of the constructs of the invention (e.g., the first and/or second populations) are included (e.g., encapsulated) at a concentration of from about $8 \times 10^6$ cells/ml to about $24 \times 10^6$ cells/ml, i.e., cells per ml of polymerizable or polymerized biomaterial (e.g., hydrogel). Cells can also, in exemplary embodiments, be engineered (e.g., genetically engineered) to express one or more "reporter proteins" to enhance detectability (e.g., colorometric, enzymatic, fluorescent, etc. detectability.)

Also included within the scope of the invention are constructs produced by the "inverse patterning", or more specifically, Intaglio-Void/Embed-Relief Topographic (InVERT) molding" methodologies of the invention. In exemplary embodiments, constructs of the invention are of a size sufficient to manipulate in a standard laboratory setting. In exemplary embodiments, a construct of the invention has a length, width, height or diameter of about 1 to about 15 cm. In other exemplary embodiments of the invention, a construct has a length, width, height or diameter of about 1 to about 150 cm. In yet other embodiments, a construct has a diameter of about 15 cm.

Also included within the scope of the invention are model animals comprising one or more construct of the invention (i.e., constructs produced by the "inverse patterning", or more specifically, Intaglio-Void/Embed-Relief Topographic (InVERT) molding" methodologies of the invention) implanted therein. Preferably, the construct are of a design appropriate to maintain significant in vivo viability and/or function over a period of time on the order of weeks or more. In exemplary embodiments, a construct remains viable in a model animal for at least three, four, six, eight or twelve weeks upon in vivo implantation. Such model animals can be particularly designed such they are models of disease.

Also featured in the invention are assay systems featuring the construct or model animals as described above. Such construct or animals can be used, for example, as a metabolic assay system or a toxicology assay system, in particular, where one of the cell populations comprised hepatocyte cells and one of the cell populations comprises stromal cells (e.g., fibroblasts or other hepatocyte supporting cells). In exemplary embodiments, the constructs or animal models of the invention are used as a screening assay system.

Also featured are uses of the constructs the invention, for implantation into a subject for therapeutic purposes, for example, in a human therapeutic method, wherein the construct is implanted into a tissue or organ of a human subject in need thereof.

So that the invention may be more readily understood, certain terms are first defined.

As used herein, the term "co-culture" refers to a collection of cells cultured in a manner such that more than one population of cells are in association with each other. Co-cultures can made such that cells exhibit heterotypic interactions (i.e., interaction between cells of populations of different cell types), homotypic interactions (i.e., interaction between cells of the same cell types) or co-cultured to exhibit a specific and/or controlled combination of heterotypic and homotypic interactions between cells.

As used herein, the term "pre-incubation" refers to a culturing or maintaining of population of cells in a manner such that cells within the population that are within sufficient juxtaposition are able to form intercellular junctions when so cultured under sufficient conditions, e.g., for a sufficient period of time. In exemplary embodiments, such "pre-incubation" occurs within a given compartment, e.g., within recesses of a substrate.

As used herein, the phrase "cell-cell junction" refers to a physical connection or junction between neighboring or adjacent cells. Preferably, "cell-cell junctions" are cadherin and/or adhesion junctions.

As used herein, the phrase "immediate trapping" refers to the physical containment or confinement of cells patterned in a substrate by initiating or triggering polymerization of biomaterial containing same without a pre-incubation period. As such, "immediate trapping" is a means to produce rapid cell patterns.

As used herein, the term "encapsulation" refers to the confinement of a cell or population of cells within a material, in particular, within a biocompatible polymeric scaffold or hydrogel. The term "co-encapsulation" refers to encapsulation of more than one cell or cell type or population or populations of cells within the material, e.g., the polymeric scaffold or hydrogel. Exemplary materials for encapsulating, for example, living cells, include hydrogels, agarose, polyethylene glycol (PEG), fibrin, and the like.

As used herein, the terms "inverse patterning" and "Intaglio-Void/Embed-Relief Topographic (InVERT) molding," are used interchangeably to refer to a methodology for patterning cells in which a first 3-dimensional, patterned material (e.g., a cell containing polymeric material) is generated, for example, using a depressed, hollowed-out or recessed mold (i.e., a patterning substrate) followed by removal from the patterning substrate and inversion of the 3-dimensional material (e.g., containing cell patterns). This methodology is also referred to as "multi-compartmental intaglio-relief (MIR) molding." This "inverse patterning" or "InVERT" or "MIR" methodology results in the exposure of an inverse pattern of the patterned depressions, recesses, and the like formed by molding of the material to the patterning substrate. In exemplary embodiments, the patterning substrate comprises a plurality of micro-scale recesses. In exemplary embodiments, the patterning substrate is a PDMS substrate. This "inverse patterning" or "InVERT" or "MIR" methodology provides for optimization of tissue structure and function in vitro and after implantation.

As used herein, the term "biochemical factor" or "biochemical cue" refers to an agent of a chemical nature having a biological activity, for example, on a cell or in a tissue. Exemplary biochemical factors or cues include, but are not limited to growth factors, cytokines, nutrients, oxygen, proteins, polypeptides and peptides, for example, adhesion-promoting proteins, polypeptides and peptides, and the like. Exemplary adhesion-promoting peptides include those derived from the extracellular matrix (ECM) of a cell or tissue, including, but not limited to collagen-derived peptides, laminin-derived peptides, fibronectin-derived peptides (e.g., the RGD-peptides), and the like.

Co-cultures can be maintained in vitro or can be included in engineered tissue constructs of the invention, maintained in vitro and/or implanted in vivo.

As used herein, the term "hydrogel" refers to a network of polymer chains that are hydrophilic in nature, such that the material absorbs a high volume of water or other aqueous solution. Hydrogels can include, for example, at least 70% v/v water, at least 80% v/v water, at least 90% v/v water, at least 95%, 96%, 97%, 98% and even 99% or greater v/v water (or other aqueous solution). Hydrogels can comprise natural or synthetic polymers, the polymeric network often featuring a high degree of crosslinking. Hydrogels also possess a degree of flexibility very similar to natural tissue, due to their significant water content. Hydrogel are particularly useful in tissue engineering applications of the invention as scaffolds for culturing cells. In preferred embodiments of the invention, the hydrogels are made of biocompatible polymers. Hydrogels of the invention can be biodegradable or non-biodegradable.

As used here, the term "parenchymal cells" refers to cells of, or derived from, the parenchyma of an organ or gland, e.g., a mammalian organ or gland. The parenchyma of an organ or gland is the functional tissue of the organ or gland, as distinguished from surrounding or supporting or connective tissue. As such, parenchymal cells are attributed with carrying out the particular function, or functions, of the organ or gland, often referred to in the art as "tissue-specific" function. Parenchymal cells include, but are not limited to, hepatocytes, pancreatic cells (alpha, beta, gamma, delta), myocytes, e.g., smooth muscle cells, cardiac myocytes, and the like, enterocytes, renal epithelial cells and other kidney cells, brain cell (neurons, astrocytes, glia cells), respiratory epithelial cells, stem cells, and blood cells (e.g., erythrocytes and lymphocytes), adult and embryonic stem cells, blood-brain barrier cells, adipocytes, splenocytes, osteoblasts, osteoclasts, and other parenchymal cell types known in the art. Because parenchymal cells are responsible for tissue-specific function, parenchymal cells express or secrete certain tissue specific markers.

Certain precursor cells can also be included as "parenchymal cells", in particular, if they are committed to becoming the more differentiated cells described above, for example, liver progenitor cells, oval cells, adipocytes, osteoblasts, osteoclasts, myoblasts, stem cells (e.g., embryonic stem cells, hematopoietic stem cells, mesenchymal stem cells, endothelial stem cells, and the like. In some embodiments stem cells can be encapsulated and/or implanted under specified conditions such that they are induced to differentiate into a desired parenchymal cell type, for example, in the construct and/or in vivo. It is also contemplated that parenchymal cells derived from cell lines can be used in the methodologies of the invention.

The term "non-parenchymal cells" as used herein, refers to the cells of or derived from the tissue surrounding or supporting parenchymal tissue in an organ or gland, for example, in a mammalian (e.g., human) organ or gland, or the connective tissue of such an organ or gland. Exemplary non-parenchymal cells include, but are not limited to, stromal cells (e.g., fibroblasts), endothelial cells, stellate cells, cholangiocytes (bile duct cells), Kupffer cells, pit cells, and the like. The choice of non-parenchymal cells used in the constructs of the invention will depend upon the parenchymal cell types used.

As used herein, the term "orthotopic" means occurring in a normal position or usual place. Accordingly, "implantation at an orthotopic site" means implantation at a normal site or at a usual site, e.g., within a tissue or organism. Exemplary implantations, for example, in human therapeutic applications, feature implanting construct comprising cells of the same type as the recipient tissue.

As used herein, the term "ectopic" means occurring in an abnormal position or place. Accordingly, "implantation at an ectopic site" means implantation at an abnormal site or at a site displaced from the normal site. Exemplary ectopic sites of implantation include, but are not limited to the intraperitoneal space and ventral subcutaneous space. Ectopic sites of implantation can also be within an organ, i.e., an organ different than that of the source cells of the construct being implanted (e.g., implanting a human liver construct into the spleen of an animal). Ectopic sites of implantation can also include other body cavities capable of housing a construct of the invention. Without being bound in theory, it is believed that that constructs implanted at in vivo survive and maintain differentiated function for significant periods of time. The term "ectopic" and "heterotropic" can be used interchangeably herein.

As used herein, the term "microscale" means on a scale on the order of microns. For example, "microscale" patterning refers to patterning having features on the order of microns (μ), e.g., patterns having features having a height, width, length, diameter, or other parameter measurable in microns, e.g., 1-5, 1-10, 2-10, 5-10, 5-50, 20-50, 10-100, 50-100, 50-500, 100-500, 200-500, 200-1000, 500-1000, less than 1000, 1-1000 microns, etc.

As used herein, the term "substrate" refers to a surface or layer that underlies something, for example, a cell, cell culture, cell culture material, etc or on which some process occurs. A "substrate" is preferable a solid substance or material, providing support to what is placed on the substrate. In exemplary embodiments, a "substrate" is a surface or material on which an organism lives, grows, and/or, optionally, obtains nourishment. As used herein, the term "substrate" also refers to a surface or layer, e.g., a base surface or layer, on which another material is deposited. Exemplary substrates include, but are not limited to glass, silicon, polymeric material, plastic (e.g., tissue culture plastic), etc. Substrates can be slides, chips, wells and the like. An exemplary substrate is polydimethyl siloxane (PDMS). Exemplary substrates are patterned, e.g., are patterned in 3D.

As used herein and in the appended claims, the singular forms "a," "and," and "the" include plural referents unless the context clearly dictates otherwise. Thus, for example, reference to "a cellular island" includes a plurality of such cellular islands and reference to "the cell" includes reference to one or more cells known to those skilled in the art, and so forth.

I. Cell Sources

The inverse patterning technology of the instant invention is readily amenable to use with a variety of cell types including primary cells, cell lines, transformed cells, precursor and/or stem cells, and the like. Exemplary embodiments feature use of parenchymal cells, optionally in combination with non-parenchymal cells, to produce engineered tissue constructs having differentiated function, e.g., for the modeling of primary tissues.

Parenchymal cells can be obtained from a variety of sources including, but not limited to, liver, skin, pancreas, neuronal tissue, muscle, and the like. Parenchymal cells can be obtained from parenchymal tissue using any one of a host of art-described methods for isolating cells from a biological sample, e.g., a human biological sample. Parenchymal cells. e.g., human parenchymal cells, can be obtained by biopsy or from cadaver tissue. In certain embodiments, parenchymal cells are derived from lung, kidney, nerve, heart, fat, bone, muscle, thymus, salivary gland, pancreas, adrenal, spleen, gall bladder, liver, thyroid, paraythyroid, small intestine, uterus, ovary, bladder, skin, testes, prostate, or mammary gland.

In exemplary aspects, the invention employs constructs containing human parenchymal cells optimized to maintain the appropriate morphology, phenotype and cellular function conducive to use in the methods of the invention. Primary human parenchymal cells can be isolated and/or pre-cultured under conditions optimized to ensure that the parenchymal cells of choice initially have the desired morphology, phenotype and cellular function and, thus, are poised to maintain said morphology, phenotype and/or function in the constructs, and in vivo upon implantation to create the humanized animals of the invention Cells useful in the methods of the disclosure are available from a number of sources including commercial sources. For example, hepatocytes may be isolated by conventional methods (Berry and Friend, 1969, J. Cell Biol. 43:506-520) which can be adapted for human liver biopsy or autopsy material. In general, cells may be obtained by perfusion methods or other methods known in the art, such as those described in U.S. Pat. Pub. No. 20060270032.

Parenchymal and non-parenchymal cell types that can be used in the above-described constructs include, but are not limited to, hepatocytes, pancreatic cells (alpha, beta, gamma, delta), myocytes, enterocytes, renal epithelial cells and other kidney cells, brain cell (neurons, astrocytes, glia), respiratory epithelium, stem cells, and blood cells (e.g., erythrocytes and lymphocytes), adult and embryonic stem cells, blood-brain barrier cells, and other parenchymal cell types known in the art, fibroblasts, endothelial cells, and other non-parenchymal cell types known in the art.

Typically, in practicing the methods of the disclosure, the cells are mammalian cells, although the cells may be from two different species (e.g., humans, mice, rats, primates, pigs, and the like). The cells can be primary cells, or they may be derived from an established cell-line. Cells can be from multiple donor types, can be progenitor cells, tumor cells, and the like. In preferred embodiments, the cells are freshly isolated cells (for example, encapsulated within 24 hours of isolation), e.g., freshly isolated cells from cadaveric donor organs. Any combination of cell types that promotes maintenance of differentiated function of the parenchymal cells can be used in the methods and constructs of the invention (e.g., parenchymal and one or more populations of non-parenchymal cells, e.g., stromal cells). Parenchymal cells which may be cultured in the constructs as described herein may be from any source known in the art, e.g., primary hepatocytes, progenitor-derived, ES-derived, induced pluripotent stem cells (iPS-derived), etc., including iPS-Heps. As used herein, the term "iPS" refers to are a type of pluripotent stem cell artificially derived from a non-pluripotent cell—typically an adult somatic cell—by inducing a "forced" expression of specific genes (traditionally Oct-3/4, SOX2, c-Myc, and Klf4; see e.g., Takahashi K, Yamanaka S (2006). Cell 126 (4): 663-76. iPS cells are similar to natural (i.e., naturally-isolated) pluripotent stem cells, such as embryonic stem (ES) cells (e.g., mouse and human embryonic stem cells, mESCs and hESCs, respectively), in many aspects, such as the expression of certain stem cell genes and proteins, chromatin methylation patterns, doubling time, embryoid body formation, teratoma formation, viable chimera formation, and potency and differentiability. Induced pluripotent cells have been made from adult stomach, liver, skin cells and blood cells. iPS cells can be induced (in a similar manner to natural (i.e., naturally-isolated) pluripotent stem cells to adopt a particular differentiated phenotype. Cells having the differentiated phenotype which are derived from iPS cells are thus termed "iPS-derived.) For example, iPS-hepatocytes are induced pluripotent stem cell-derived hepatocyte-like cells.

Use of pluripotent cells in in vitro model systems and cell-based therapies requires understanding and control over human development. Multi-factorial signals (e.g., cell contact, paracrine signals, extracellular matrix) contribute to the development of tissues such as the liver bud, but methodical dissection of their relative contributions in 3D settings has been hampered by the complexity of traditional animal model systems. Described herein is the creation of novel 3D model systems that are scalable for clinical applications. This platform combines multicellular 3D micropatterning in biomaterials, genetic reporter systems, high-resolution 3D imaging, and automated image analysis. It has been found that the inclusion of stromal cells upon aggregate formation augments hepatic function of iPS-Heps. These interactions likely occur via local paracrine or direct contact signals since intimate contact between iPS-Heps and stromal cells is required throughout the entire aggregate ('interpenetrating' conformation) and patterning of stromal cells at the external periphery of the aggregate ('juxtaposed' conformation) is inadequate to stimulate enhanced function. The molecular mechanisms regulating these interactions possibly include short range molecular mediators such as those that mediate interactions between adult primary hepatocytes and J2 stromal cells, e.g., decorin and truncated-cadherin, and these could similarly impact iPS-Hep function (Khetani, S. R., et al. *Hepatology* 40, 545-554 (2004) and Khetani, S. R., et al. *FASEB J* 22, 3768-3775 (2008)). The studies described in the working examples suggest that InVERT molding may be useful in studies that probe differentiation state or signaling pathway activity of stem cell progeny or tissue organoids.

Further cell types which may be cultured in the constructs of the invention include pancreatic cells (alpha, beta, gamma, delta), enterocytes, renal epithelial cells, astrocytes, muscle cells, brain cells, neurons, glia cells, respiratory epithelial cells, lymphocytes, erythrocytes, blood-brain barrier cells, kidney cells, cancer cells, normal or transformed fibroblasts, liver progenitor cells, oval cells, adipocytes, osteoblasts, osteoclasts, myoblasts, beta-pancreatic islets cells, stem cells (e.g., embryonic stem cells, hematopoietic stem cells, mesenchymal stem cells, endothelial stem cells, etc.), cells described in U.S. patent application Ser. No. 10/547,057 paragraphs 0066-0075 which is incorporated herein by reference, myocytes, keratinocytes, and indeed any cell type that adheres to a substrate.

It is understood that constructs of the invention may contain parenchymal cells with one, or two or more types of non-parenchymal cells such as, for example, stromal cells, endothelial cells, etc. One of skill in the art will appreciate that particular patterns of non-parenchymal cells and/or parenchymal cells may be desired in some cases, e.g., when it is desired to mimic certain in vivo environments. It is understood that any support or accessory cells may be included in the constructs of the invention.

In exemplary embodiments of the invention, supporting or accessory non-parenchymal cells can serve to enhance vascular recruitment to the constructs of the invention. For example, non-parenchymal cells can be selected for encapsulation in the constructs of the invention based on their ability to secrete one or more pro-angiogenic factors. Exemplary pro-angiogenic factors include, but are not limited to vascular endothelial growth factor (VEGF), including isoforms A, B, C, and D, basic fibroblast growth factor (bFGF), interleukin-6 (IL-6), and other inflammatory cytokines, tumor necrosis factor alpha (TNFα), hepatocyte growth factor (HGF) and the like. Non-parenchymal cells can be selected that secret such factors, or can be engineered (e.g., recombinantly engineered) to secrete such factors.

In exemplary embodiments of the invention, vascular endothelial cells are included in the constructs of the invention, e.g., to support parenchymal cells, in particular, hepatic cells. Vascular endothelial cells play important roles in tissue development, homeostasis, and function in health and disease (Matsumoto, K., *Science* 294, 559-563 (2001); Cleaver, O., et al. Nat Med 9, 661668 (2003); Ding, B. S., et al. *Nature* 468, 310-315 (2010); Franses, J. W., et al. Sci Transl Med 3, 66ra65 (2011); and Ding, B. S., et al. *Cell* 147, 539-553 (2011)). Indeed, inclusion of endothelial and mural cells in engineered tissues has been shown to greatly enhance graft survival (Ding, B. S., et al. *Cell* 147, 539-553 (2011) and Levenberg, S., et al. *Nat Biotechnol* 23,879-884 (2005)). In the experiments described in the working examples, it was found that the structural organization of these cells, e.g., liver endothelial cells, modulates the degree to which they support and stabilize hepatic parenchyma. Without being bound in theory, it is believed that endothelial cell organization alters tissue function in exemplary InVERT systems of the invention. Possible mechanisms include hepatic interaction with inhibitory endothelial cell surface molecules (e.g., cadherin), extracellular matrix molecules, and/or short-range or matrix-sequestered soluble factors in juxtaposed but not paracrine conformation.

Without being bound in theory, it is also contemplated that one or more soluble factors could be included in a construct of the invention, for example, in drug delivery vehicle (e.g., encapsulated in a drug delivery particle, for example, a time-released delivery particle.)

In certain embodiments, the constructs are engineered to include one or more adherence materials to facilitate maintenance of the desired phenotype of the encapsulated cells. The term "adherence material" is a material incorporated into a construct of the invention to which a cell or microorganism has some affinity, such as a binding agent. The material can be incorporated, for example, into a hydrogel prior to seeding with parenchymal and/or non-parenchymal cells. The material and a cell or microorganism interact through any means including, for example, electrostatic or hydrophobic interactions, covalent binding or ionic attachment. The material may include, but is not limited to, antibodies, proteins, peptides, nucleic acids, peptide aptamers, nucleic acid aptamers, sugars, proteoglycans, or cellular receptors.

The type of adherence material(s) (e.g., ECM materials, sugars, proteoglycans etc.) will be determined, in part, by the cell type or types to be cultured. ECM molecules found in the parenchymal cell's native microenvironment are useful in maintaining the function of both primary cells and precursor cells and/or cell lines. Exemplary ECM molecules include, but are not limited to collagen I, collagen III, collagen IV, laminin, and fibronectin.

In certain embodiments, improved performance can result from a combination of appropriate heterotypic contacts, for example, between parenchymal cells and at least one population of non-parenchymal cells and soluble biochemical cues (e.g., supporting parenchymal cell phenotype and function and, optionally, additionally promoting vaccularization.) Parenchymal cell stabilizing cues and proangiogenic cues can come from the same, or from different populations of non-parenchymal cells. Additional stabilizing cues can include, for example, certain cell-surface molecules, cadherins, receptor ligands, and the like (see, in particular, Khetani et al. 2004, Hepatology 40(3): 545-554, the content of which is hereby incorporated by reference.

Small "aggregates" of cells can be used in the method of the invention, for example, aggregates of about 5-10, 10-100, 5-100. 10-500, 50-500 cells, etc. "Aggregates" can comprise one cell type, i.e., "homo-aggregates" or diverse cell types, i.e., "hetero-aggregates".

Cells, e.g., cells of differing cell types, can be cultured in different "compartments" of the micropatterned substrates of the invention. Alternatively, or in combination, cells of differing cell types can be co-cultured within "compartments" of the micropatterned substrates of the invention.
Deficiencies in Art-Recognized Patterning Technologies A severe shortage of functional human tissues precludes clinical transplantation for most organ failure patients. Artificial organs and tissues may offer alternatives or bridges to organ transplant. To date, engineered tissues that have been applied clinically (e.g., bladder and skin) (MacNeil, S., *Nature* 445, 874-880 (2007); Atala, A., *Curr Opin Biotechnol* 20, 575-592 (2009)) contain few cell types and have simple organizational structure. In contrast, construction of complex, highly metabolic tissues such as liver, kidney, and heart has seen little success (Mikos, A. G., et al. *Tissue Eng* 12, 3307-3339 (2006)). Complex tissues are spatially organized across functionally and morphologically distinct but interacting compartments (e.g., the parenchyma and vasculature). At the microscale, these compartments are often arranged with precise microstructural control in locally-repeated functional units (e.g., a hepatic cord and associated sinusoid). Such hierarchical positioning of cells within the tissue, or 'tissue architecture,' ultimately defines the cell-cell contacts and paracrine signaling gradients that drive cellular phenotype and function of each tissue unit, and the collective activity contributed by all units yields large-scale physiologic tissue function. Construction of complex engineered tissues requires an understanding of how multicompartmental tissue architecture dictates whole tissue function both in vitro and after implantation. For such experiments, engineered tissues must be of adequate mass (contain many repeating microscale tissue units) to generate robust functions measureable by tissuelevel experiments and/or to result in a therapeutic outcome. To date, the ability to rapidly organize multiple cell types with microscale precision into units that combine to generate tissues of scalable sizes has remained elusive.

To pattern cells in three-dimensional (3D) engineered tissues, dielectrophoresis and photopatterning, including two-photon-based photochemical and photomechanical patterning, have been explored (Albrecht, D. R., et al. *Nat Methods* 3, 369-375 (2006); Liu Tsang, V., et al. *FASEB J* 21, 790-801 (2007); Underhill, G. H., et al. *Biomaterials* 28, 256-270 (2007); Wylie, R. G., et al. *Nat Mater* 10, 799-806 (2011); Culver, J. C., et al. *Adv Mater* 24, 2344-2348 (2012); Kloxin, A. M., et al. *Science* 324, 59-63 (2009); and DeForest, C. A., et al. *Nat Chem* 3, 925-931 (2011)). However, these approaches are difficult to scale to tissues of large size, compatible only with materials of highly specific properties (i.e., proper conductivity or polymerization trigger), non-physiologic by exposing cells to potentially detrimental stimuli (i.e., electricity and UV light), and dependent upon specialized equipment, which precludes broad technological dissemination. Bioprinting has also been explored but requires tedious serial deposition of cells, and thus generation of tissues with both large mass and repetitive high-resolution microscale tissue architecture for large biologic studies is not feasible (Mironov, V., et al. *Biomaterials* 30, 2164-2174 (2009) and Jakab, K., et al. *Biofabrication* 2, 022001 (2010)). Additionally, like dielectrophoresis and photopatterning, bioprinting also requires specific material systems, exposes cells to detrimental forces (shear), and requires specialized equipment. Bioprinting 3D filament networks as sacrificial templates circumvents some of these issues, but this process has not been yet been extended for micropatterning multicellular tissues (Miller, J. S., et al. *Nat Mater* 11, 768-774 (2012)). An alternative would be to pattern cells in parallel using topographic surfaces with microscale features (Nelson, C. M., et al. *Science* 314, 298-300 (2006) and Tekin, H., et al. *J Am Chem Soc* 133, 12944-12947 (2011)) and then subsequently embed patterned cells within a single freestanding hydrogel via 'topographic molding' (Rago, A. P., et al. *Tissue Eng Part A* 15, 387-395 (2009)). This method addresses cell compatibility concerns, but to date has been used only to generate free-standing gels of a single cell type in a given tissue layer. Organization of varied cell types across distinct compartments using this method would require fabrication of multiple layers followed by tedious manual alignment. Together, these issues have severely limited the application of existing methods to answering basic biological questions as well as building scaled tissues for clinical translation.

III. Methods of Making Constructs—Inverse Patterning

The present invention features processes by which to encapsulate multiple cell types with distinct organization into three-dimensional structures. This "inverse patterning" or "MIR" or "InVERT" methodology improves over the art-recognized patterning technologies in several important aspects.

Here, it was sought to create a platform that 1) enables precise organization of microscale and multi-compartmental tissue structure within tissues of sizes relevant for in vitro, pre-clinical, and clinical studies, and 2) is both material- and cell type-independent and therefore widely biologically applicable. The 'Intaglio-Void/Embed-Relief Topographic (InVERT) molding' process described here produced engineered tissues up to 14 cm in diameter, resulted in viable and high-resolution microstructures organized in distinct compartments in several multicellular patterns, was compatible with fibrin, agarose, and polyethylene glycol hydrogel systems, and could be used to pattern a variety of cell types, including fragile cell types such as induced-pluripotent stem cell derived hepatocyte-like cells (iPS-Heps), which have not been patternable to date (Schwartz, R. E., et al. *Proc Natl Acad Sci USA* 109, 2544-2548 (2012) and Si-Tayeb, K., et al. *Hepatology* 51, 297-305 (2010)).

The InVERT technology was applied to probe issues relevant to the translation of engineered liver tissue to the clinic. Specifically, crosstalk between hepatocytes and non-parenchymal cells has been implicated in development, physiological homeostasis, regeneration, and disease (e.g., malignant transformation) (Matsumoto, K., *Science* 294, 559-563 (2001); Cleaver, O., et al. *Nat Med* 9, 661668 (2003); Ding, B. S., et al. *Nature* 468, 310-315 (2010); and Bhatia, S. N., et al. *FASEB J* 13, 1883-1900 (1999)), but systematic dissection of 3D structure-function cellular relationships has proven challenging due to the lack of robust model systems. To more precisely elucidate these relationships, InVERT molding was used to test whether manipulation of tissue architecture modulates physiologic function of primary rat and human hepatocytes or human iPS-Heps in vitro and following implantation in rodents. It was found that placement of nonparenchymal cells with respect to primary or iPS-derived hepatocytes and optimization of hepatic compartment microstructure and composition modulates hepatic functions. Additionally, architectural configurations found to sustain hepatic function in in vitro studies also resulted in prolonged survival and physiologic function in model animals, e.g., nude mice, after transplantation (see section V, infra). These results demonstrate the need for the optimization of microstructural architecture in constructing physiologically robust model systems and engineered tissue therapies.

Previous technologies such as dielectrophoresis, photo-patterning, laser printing, and cell 'bioprinting' have achieved multi-cellular tissue patterning, but the biological application of these technologies has been limited by technical parameters of the systems. For example, many of these patterning technologies necessitate the use of 'immediate trapping' of cells in a biomaterial without prior cell-cell pre-aggregation, which results in low cellular density in microstructures and interferes with the formation of intercellular junctions that are critical for normal physiologic function in many tissues. Additionally, technological compatibility with a narrow range of materials systems as well as exposure of cells to potentially damaging external physical forces (e.g., electricity, UV light, and mechanical forces) have limited dissemination to the biological community. Finally, challenges in scalability resulting from the need to micro-pattern each cell type in a separate hydrogel layer followed by manual merger (e.g., in dielectrophoresis) or to make trade-offs between printing time and resolution (e.g., in bioprinting) has limited the generation of adequate tissue numbers necessary for large-scale physiologic in vitro and in vivo studies for identifying functionally optimal tissue architectures.

The "inverse patterning" or "InVERT" or "MIR" molding platform presented herein is a versatile process that yields high-resolution multi-cellular microstructures that can be patterned in distinct compartments in 3D hydrogels. InVERT molding offers several advantages over previous patterning systems. First, substrate-based molding is scalable and can produce tissue sizes ranging over two orders of magnitude without significantly altering microstructure resolution or assembly-time. Second, this process can be used to pattern cells via 'pre-incubation' (preaggregated cells) to enable the formation of intercellular junctions in a given compartment (necessary for normal physiologic function in most tissues) as well as by immediate 'trapping', akin to other patterning technologies (e.g., dielectrophoresis) to produce rapid cell patterns. Third, the InVERT molding process does not necessitate tedious manual alignment of cell layers and can be parallelized and is therefore rapid and facile. Fourth, this method is compatible with patterning substrates (e.g., customizable topographic patterning substrates) and material systems (e.g., PEG) employed in specialized engineering and biomaterials research laboratories and as well as with materials found routinely in basic biological laboratories (e.g., agarose or fibrin) as well as highly-tunable and customizable materials (e.g., PEG) found in specialized engineering and chemistry laboratories. Indeed, any biomaterial that can efficiently mold and retain microscale features is compatible with this process. Fourth, InVERT molding is based simply on gravity or centrifugation-enhanced cellular sedimentation and therefore invokes minimal damage to cells, even to otherwise sensitive cell types. Finally, InVERT molding enables the multi-level hierarchical optimization of tissue structure both within and between cellular compartments. Indeed, in this work both the relative placement of a second distinct vascular compartment as well as the microstructure and cellular composition within the parenchymal compartment is controlled. Together, these features of InVERT molding uniquely enabled large-scale tissue production for physiologic tissue optimization studies. In particular, these features of InVERT molding uniquely enable large-scale biological studies that probe how complex tissue structure dictates cellular behavior.

In preferred embodiments of the instant invention, cells are first arranged into desired physical patterns using, for example, molds suited to cell culture. A preferable process features the use of polydimethyl siloxane (PDMS) molds, patterned with micro-scale features, e.g., microscale features that mimic in vivo cellular patterns.

Such molds are referred to herein as "cell-capture substrates" and can be made according to any art-recognized process for generating same.

Cells, e.g., a first population of cells, are introduced into "cell-capture substrates", for example, in media or in a pre-polymer material (e.g., a polymerizable hydrogel in the absence of initiator.). Cells, e.g., a first population of cells, patterned in media are then incubated under conditions sufficient to allow formation of cell-cell junctions, e.g., cadherin and adhesion junctions. Such conditions can include culturing in a standard cell culture environment for a time sufficient to form cell-cell junctions. In exemplary embodiments, this time is from about 6 to about 24 hours, e.g., about 8 to about 16 hours, e.g., about 12 hours. Such cells are then encapsulated in a biomaterial, a step referred to alternatively herein as pre-incubation. Cells in pre-polymer are trapped directly or immediately after patterning by initiating or "triggering" material polymerization. Such a step can be referred to as "trapping." 3D materials containing cell patterns are then removed from the patterning substrate and inverted, resulting in the exposure of an "inverse pattern" of the recesses, e.g., micro-scale recesses, formed by molding of the material to the cell capture substrate, e.g., the PDMS substrate. A second cell population is then loaded, within a polymerizable biomaterial solution, to produce an inverse pattern. Polymerization is then initiated or "triggered" to trap and encapsulate the second population of cells. This process results in the formation of a single 3D biomaterial gel system containing two different micropatterned cellular compartments. This process can produce a variety of multi-cellular patterns in multiple material systems. The working examples appended hereto feature encapsulating cells in agarose, fibrin, and polyethylene glycol hydrogels using this approach, although other biomaterials are clearly suitable. For example, biodegradable biomaterials can be used in the methodology of the invention. In this regard, polylactic acid (PLA) is commonly used synthetic biomaterial for tissue engineering applications. This polyester degrades within the human body to form lactic acid, a naturally occurring chemical which is easily removed from the body. Similar materials are polyglycolic acid (PGA) and polycaprolactone (PCL): their degradation mechanism is similar to that of PLA, but they exhibit respectively a faster and a slower rate of degradation compared to PLA.

The methodologies of the invention are readily scalable for a variety of uses. Constructs, e.g., hydrogels of from about 1 cm up to about 15 cm in diameter have been constructed with clear potential for generating constructs e.g., hydrogels of significantly increased sizes. As will be appreciated by the skilled artisan, smaller constructs are often more suited to animal applications (e.g., rodent animal model applications) whereas larger constructs are often more suited, for example to primate animal model applications, human therapeutic applications, and the like.

IV. Engineering tissues for Human Therapeutic Use

The methodology of the instant invention is particularly suited for use in aspects of tissue engineering. The studies presented herein describe the development and characterization of a platform technology useful to precisely micro-organize multiple cell types in distinct cellular compartments within 3D hydrogels. This platform is robust, versatile, and scalable to engineered tissues sizes relevant for human therapy. The data presented herein demonstrate that this system can be used for investigating increasingly complex biological aspects of 3D tissue systems. The results indicate that high-fidelity and hierarchical micro-organization of hepatocyte, mural, and endothelial cells across two distinct 'parenchymal' and 'vascular' cellular compartments dictates physiologic tissue function of engineered liver tissue. Importantly, optimal tissue assembly also modulates tissue survival and function following implantation. Together, the results presented herein demonstrate the biological and clinical relevance of multi-level optimization of multi-compartmental placement, microstructure, and multi-cellular composition in the construction of engineered tissues or "tissue engineering."

The term "tissue engineering" refers the use of a combination of cells, engineering and materials methods, and suitable biochemical and physio-chemical factors to improve or replace biological functions in a subject in vivo. While it was once categorized as a sub-field of bio materials, having grown in scope and importance it can be considered as a field in its own right.

In particular, the term "tissue engineering" refers to applications that repair or replace portions of or whole tissues (e.g., bone, cartilage, blood vessels, bladder, skin etc.). Often, the tissues involved require certain mechanical and structural properties for proper functioning. The term has also been applied to efforts to perform specific biochemical functions using cells within an artificially-created support system (e.g., an artificial pancreas, or a bio artificial liver). Tissue engineering featuring the use of stem cells is often referred to as "regenerative medicine."

The clinical utility of engineered tissues will ultimately be dictated by the ease with which these tissues can be scaled to sizes relevant for human therapy. Complex and expensive patterning technologies reduce translation efficiency of engineered tissue systems by complicating scaling of tissue size and production. Indeed, most technologies previously used to pattern cells in engineered tissues have resulted in tissues that are approximately 1 cm in diameter. The data presented herein demonstrates that the substrate-based molding approach of the instant invention is highly efficient and can be scaled to tissue sizes that are relevant for human therapy.

Various cells sources, as described above, can be use in the methodology of the instant invention. For human therapeutic use, cells can further be selected as follows. Autologous cells are obtained from the same individual to which they will be reimplanted. Autologous cells have fewer problems with rejection and pathogen transmission, however in some cases might not be available (e.g., when treating genetic disease, treating very ill or elderly persons, treating patients suffering from severe burns, etc., where it may not be possible to obtain sufficient quantities of autologous cells to establish useful cell lines. Autologous cells also include, for example, mesenchymal stem cells from bone marrow and fat of the individual. Such cells can differentiate into a variety of tissue types, including bone, cartilage, fat, and nerve. A large number of cells can be easily and quickly isolated from fat, thus opening the potential for large numbers of cells to be quickly and easily obtained.

Allogeneic cells come from the body of a donor of the same species, for example, dermal fibroblasts from human foreskin, umbilical cells, etc. Xenogenic cells are these isolated from individuals of another species, for example non-human mammalian cells used in human therapeutic applications. Syngenic or isogenic cells are isolated from genetically identical organisms, such as twins, clones, or highly inbred research animal models. Primary cells are from an organism. Secondary cells are from a cell bank. Stem cells are undifferentiated cells with the ability to divide in culture and give rise to different forms of specialized cells. According to their source stem cells are divided into "adult"

and "embryonic" stem cells, the first class being multipotent and the latter mostly pluripotent; some cells are totipotent, in the earliest stages of the embryo.

It should be noted that the studies described herein demonstrate the organization of three cell types across two distinct compartments. In further embodiments, additional cell types can be added to each compartment via the addition of further cell seeding and incubation steps. Moreover, coupling of InVERT molding with other 'top-down' and 'bottom-up' approaches can be used to enhance tissue organizational complexity. For example, the addition of layer-by-layer hydrogel assembly or bioprinting to the processes exemplified herein can enable the construction of additional cellular compartments.

It should also be noted that in InVERT molding processes exemplified herein, the resolution of patterned microstructures is dictated by poisson distribution of cellular sedimentation into the features of the patterning substrate. Microstructure resolution of several cells per microstructure can therefore easily be achieved and patterning can indeed be performed at the single cell level, but poisson distribution ultimately dictates the exact tissue location of each cell. To address this issue, combination of InVERT molding with other techniques such as bioprinting and scaffold-free technologies can have powerful implications for rapidly creating high-resolution and high-density multi-cellular tissues with multiple compartments.

V. Model Animals Having Engineered Constructs Implanted Therein

The methodology of the invention is also particularly suited for use in animal systems, for example, for basic research, modeling disease states, testing potential drug compounds in vivo, toxicology screening, and the like. As used herein, the term "animal model or "model animal" (used interchangeably herein) refers to a living, non-human animal used during the research and investigation of human physiology and/or disease, for the purpose of better understanding the physiology and/or disease without the added risk of causing harm to an actual human being during the process. In exemplary embodiments, the invention features constructs in which cells are patterned to achieve a high degree of similarity to a chosen in vivo system. For example, constructs featuring parenchymal cells or highly differentiated cells can be patterned to mimic the physiologic properties of the corresponding or source tissue from which the cells are derived. In certain embodiments, the function of parenchymal or highly differentiated cells is enhanced in constructs of the invention by choosing particular combinations of parenchymal and/or non-parenchymal cells, for example, parenchymal cells and stromal cells (e.g., fibroblasts.) Combinations of cells can be patterned at distinct locations within the constructs of the invention and/or within the same locations within the constructs (e.g., to facilitate cell-cell junctions forming between distinct cell types.) In exemplary embodiments, the constructs feature cell populations patterned to mimic interactions between cells (e.g., cell junctions) involved in the organization of tissues in vivo.

Exemplary model animals include animals having implanted therein constructs of the invention comprising pancreatic cells (alpha, beta, gamma, delta), enterocytes, renal epithelial cells, astrocytes, muscle cells, brain cells, neurons, glia cells, respiratory epithelial cells, lymphocytes, erythrocytes, blood-brain barrier cells, kidney cells, cancer cells, normal or transformed fibroblasts, liver progenitor cells, oval cells, hepatocytes, adipocytes, osteoblasts, osteoclasts, myoblasts, beta-pancreatic islets cells, stem cells (e.g., embryonic stem cells, hematopoietic stem cells, mesenchymal stem cells, endothelial stem cells, etc.), and the like.

In one exemplary embodiment, the invention features animals implanted with constructs in which hepatocytes are patterned therein. Such animals have particular use, for example, in toxicology testing, study of hepatic disease, drug testing and the like.

VI. Uses

The methodology and constructs of the invention are useful in a number of different methods as set forth in more detail below.

This platform technology is anticipated to have utility in the development of engineered tissues for human therapies, drug testing, and disease models. It is proposed that this technology will be particularly useful for enabling higher fidelity construction of complex organ engineered tissue and model systems such as liver and heart, which are notably the tissue-types most relevant for drug toxicity screening by pharmaceutical companies (e.g., for testing novel compounds for biocompatibility). Additionally, it is envisioned that this platform to be useful in basic science research. Specifically, the engineered constructs can serve as model systems for studying 3D cell-cell interactions in diverse fields ranging from stem cell to cancer biology. The rapid and facile construction of multi-cellular tissues using this approach enables multi-cellular 3D patterning to be combined with a variety of screening applications (e.g., genetic model systems, RNAi screens). In summary, this technology allows studies of engineered tissues and multi-cellular model systems of both complexity and scale that are precluded by current technologies and methods.

It should be noted that the micro-scale cellular patterns exemplified herein are relevant across a broad range of biological fields. Cellular aggregates are widely used for studying 3D cellular interactions in stem cell biology, tissue morphogenesis, and disease model systems such as cancer (Ungrin, M. D., et al. *PLoS One* 3, e1565 (2008); He, J. Q., et al. *Circ Res* 93, 32-39 (2003); Zhang, S. C., et al. *Nat Biotechnol* 19, 1129-1133 (2001); Inman, J. L. & Bissell, M. J. *J Biol* 9, 2 (2010); and Mailleux, A. A., et al. *Cell Cycle* 7, 57-62 (2008)). Organized lattice structures are prevalent in human tissue organization (e.g., cancellous bone, muscle fiber structure, and the vascular tree). It is envision that the InVERT molding technology of the instant invention has applicability in engineering a multitude of tissues having such organization. The use of InVERT molding in other fields such as stem cell or cancer biology is also envisioned.

EXAMPLES

The following examples demonstrate the ability to modulate both microstructure and multi-cellular composition within a given tissue compartment. In particular, these data demonstrate the importance of the structural and multi-cellular optimization of parenchymal cell units in engineered tissues.

To demonstrate the power of the specific molding techniques of the invention, a system was developed that enables both patterning of distinct 'parenchymal' and 'vascular' compartments as well as hierarchical fine-tuning of the micro-structure and multi-cellular composition within a given compartment in engineered liver tissue.

It had been previously shown that encapsulation of primary hepatocytes distributed homogeneously in 3D engineered tissues immediately following isolation resulted in hepatocyte death (Underhill, G. H., et al. *Biomaterials* 28, 256-270 (2007)). It was reasoned that anoikis was contributing to cell death and that precise control of intercellular contacts in cultures the might improve hepatic functions of engineered liver tissues. Accordingly, a system was developed that enables the formation of intercellular contacts prior to patterning as well as 'fast-trapping' of cells immediately following patterning.

The 'Intaglio-void/embed-Relief Topographic (InVERT) molding' process described in the following examples is a versatile, robust, and scalable platform that enables precise multi-level optimization of tissue structure both between and within cellular compartments in a single monolithic hydrogel. The InVERT molding' process produces high-resolution multi-cellular microstructures across distinct compartments, greatly reduces the need for specialized equipment and tedious protocols, and is compatible with both widely available and highly tunable patterning templates and material systems. The following examples use this system to test whether placement of distinct parenchymal and vascular compartments as well as hierarchical micro-organization and multi-cellular composition within a given compartment dictates physiologic tissue function of engineered liver tissue. It is shown that each of these factors impacts hepatic tissue function and, importantly, that optimal tissue assembly dictates tissue survival and function following implantation.

Example 1

Fabrication of Exemplary Inverse Patterned Constructs—InVERT Molding to Fabricate Engineered Tissues with Distinct Multicellular Micro-compartments The present invention features a process by which to encapsulate multiple cell types with distinct organization into a 3D hydrogel. (FIG. 1a). In particular, scalable, versatile, and rapid 3D multi-compartmental cellular patterning was achieved using an InVERT molding protocol (FIG. 1a). Topographic substrates were first produced containing microscale features and replica molded these substrates using poly(dimethylsiloxane) (PDMS) to create topographic 'intaglio' cell capture substrates with recessed 'voids'. In this example, cells were first isolated in the micro-scale features of polydimethyl siloxane (PDMS) cell-capture substrate either in media or in a pre-polymer material. Cells patterned in media were then incubated overnight to allow formation of cell-cell junctions, e.g., cadherin and adhesion junctions, and then encapsulated in a biomaterial, a step referred to herein as pre-incubation. Alternatively, cells in pre-polymer were trapped immediately after patterning by triggering material polymerization, a step referred to herein as immediate trapping. 3D materials containing cell patterns were then removed from the patterning substrate and inverted, resulting in the exposure of an "inverse pattern" or "multi-compartmental intaglio-relief mold" of micro-scale recesses formed by molding of the material to the PDMS substrate. A second cell population was then loaded within a prepolymer solution to produce an inverse pattern, and polymerization was triggered to trap and encapsulate cells. This process resulted in the formation of a single 3D biomaterial gel system containing two different micropatterned cellular compartments. This process can produce a variety of multi-cellular patterns in multiple material systems (FIG. 1b). The instant examples feature encapsulating cells in agarose, fibrin, and polyethylene glycol hydrogels using this approach. This process is readily scalable. Constructs, e.g., hydrogels of from about 1 cm up to about 15 cm in diameter have been constructed with clear potential for generating constructs e.g., hydrogels of significantly increased sizes (FIG. 1c).

In detail, efficient 3D multi-compartmental and microscale cellular patterning was accomplished using a facile InVERT molding protocol (FIG. 1a). Masters were first produced with micro-scale features by selective anisotropic etching of silicon or computer numerical control milling of high-temperature epoxy. The masters were then replica molded using polydimethyl siloxane (PDMS) to create 'intaglio' cell capture substrates with recessed features.

Cells were isolated in the features of the intaglio cell-capture substrate in either media or in a pre-polymer material. Cells were added in solution, isolated in the features of the intaglio cell-capture substrate via centrifugation or sedimentation, and then embedded within a 3D hydrogel. For example, cells patterned in media were incubated overnight to allow formation of cadherin and adhesion junctions and then encapsulated in a biomaterial ('pre-incubation'). Alternatively, cells in pre-polymer were trapped immediately after patterning by triggering material polymerization ('trapping'). Molded 3D materials, e.g., hydrogels, containing cell patterns were then removed from the intaglio patterning substrate and inverted, resulting in the exposure of a 'relief', effectively the inverted intaglio geometry, in which microscale features containing the first cell population projected from the hydrogel. A second cell population within pre-polymer solution was loaded on top of the inverted hydrogel (which serves as a secondary mold) and centrifuged into the features of the relief such that the second cell population inter-wove with the first cell population through a single Z-direction plane. Polymerization was then triggered to trap and encapsulate cells, yielding a 3D hydrogel containing multiple micropatterned cellular compartments. This process resulted in the formation of a single monolithic 3D biomaterial hydrogel system containing two micro-patterned cellular compartments.

Figure 5A:
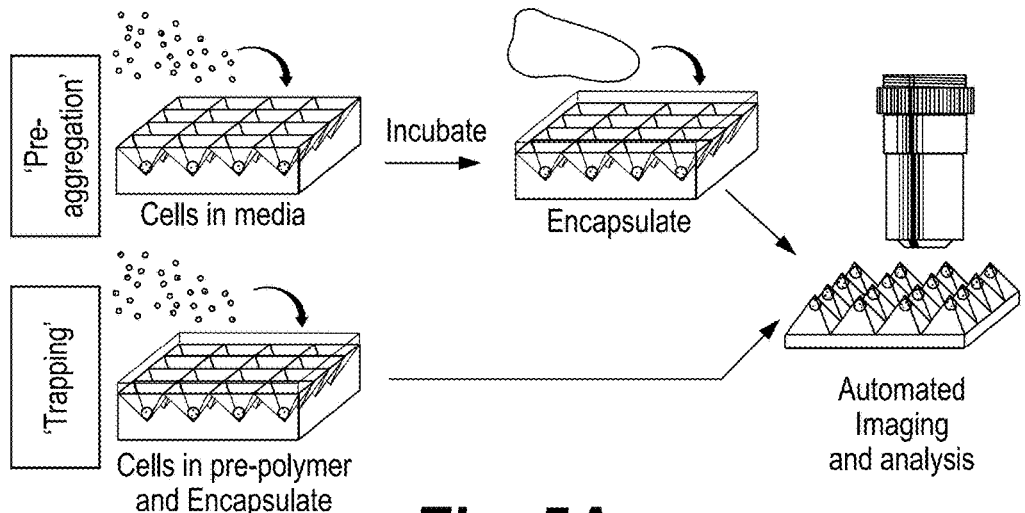
FIG. 5. Substrate-based molding is highly efficient and compatible with both 'pre-incubation' and 'immediate trapping' methods (a) Schematic depicting formation of hydrogels containing hepatocyte aggregates. (b) An automated platform to image and analyze microstructure size and patterning efficiency was developed (scale bar 1 mm). Here, a representative image of a patterned hydrogel is shown after image analysis. (c) Quantification of patterning efficiency of gels fabricated after 'pre-incubation' (left) of cells to allow formation of intercellular junctions or via immediate 'trapping' (right) reached 97±1% in optimal conditions. Box plot whiskers denote minimum to maximum values.
Figure 5B:
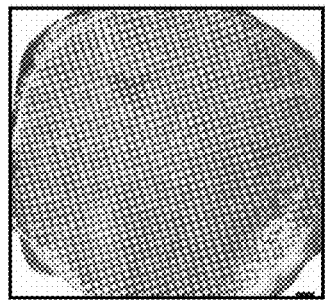
Figure 5C:
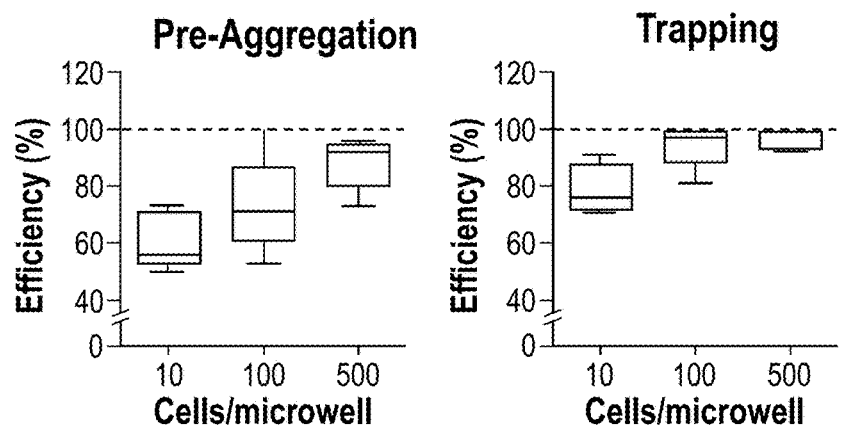

Since InVERT molding relies on substrate-based molding, the efficiency, flexibility, and scalability of substrate-based molding was first tested. Organized arrays of hepatocyte clusters within 3D hydrogels were created by molding from a PDMS patterning substrate containing pyramidal microwells (Ungrin, M. D., et al. *PLoS One* 3, e1565 (2008)) either after 'pre-incubation' or via immediate 'trapping' (FIG. 5a). Scalable gels must also demonstrate fidelity in patterning. We assayed 'patterning efficiency', or the percentage of microstructures (here aggregates) successfully patterned in a macroscopic hydrogel upon its removal from the topographic patterning substrate. In order to detect and count the aggregates present within each hydrogel, a high-throughput method for automated large-image scanning, imaging, and analysis of cellular microstructures in engineered tissues was developed (FIG. 5a-b). Patterning efficiency was assayed when 1) cells in media were patterned in the topographic microwell substrate, incubated overnight to promote cadherin and adhesion junction formation, and then embedded in a hydrogel, or 2) cells in a pre-polymer solution were added to the topographic mold and trapped immediately by triggering hydrogel polymerization. For hydrogels created with a pre-incubation step, the percentage of clusters successfully retained in the hydrogel gel upon removal of the hydrogel from the patterning substrate ('patterning efficiency') improved with feature size (FIG. 5c) and reached an average of 88±4%. Immediate trapping of cells resulted in patterning efficiency that was 78±4%, 94±3%, and 97±1% for 10, 100 and 500 cells per microwell, respectively (FIG. 5b). Thus, substrate-based molding is efficient and compatible with both pre-aggregation and rapid trapping methods.

The clinical utility of engineered tissues is ultimately be dictated by the ease with which these tissues can be scaled to sizes relevant for human therapy. Therefore, it was next sought to fabricate hydrogels with patterned microstructures at various macroscopic size scales. Here, the individual size and spacing (800 μm) of distinctly patterned cellular clusters was increased to enable visualization of cellular patterns by naked eye after hematoxylin staining. Arrays of cellular microstructures were patterned within hydrogels to construct tissues with diameters that varied across two orders of magnitude. Sizes of the smallest producible hydrogels were constrained only by the resolution of photopatterning and microfabrication methods. Micro-patterned tissues or intermediate size (1.5 cm diameter) were engineered for subsequent in vitro and mouse studies (FIG. 1b, inset). Finally, this process was scaled to build tissues of clinically-relevant size up to 14 cm in diameter (FIG. 1b). Despite increased cluster size and spacing for visualization, a robust array of over 24,000 cellular aggregates in the 14 cm-diameter tissue was produced. In this large scale example, cell cluster size and wider spacing allowed for macroscopic detection of cellular patterns after hematoxylin staining, and tissues contained over 24,000 arrayed cellular aggregates. These clusters are patterned in a single molding step (rather than serially). Therefore, cluster spacing could be reduced without altering tissue size and the cellular constitution of all clusters is representative of the cell types included in the initial patterning solution. Downscaling of cluster spacing to 400 μm, the size used throughout the remainder of the working examples, results in over 96,000 cellular clusters per tissue of this size. Together, these studies demonstrate that substrate-based molding enables the construction of scalable engineered tissues with high microstructure patterning fidelity.

To illustrate the capabilities and versatility of InVERT molding for multi-cellular and multi-compartmental cellular patterning, it was desired to utilize patterning substrates that were either 1) inexpensive and readily available, 2) high-precision and commercially available, or 3) custom-produced using specialized engineering technologies. Endothelial cells (green) and fibroblasts (red) were thus organized in various different distinct patterns using custom-fabricated substrates with complex topographies ((substrates fabricated via computer numerical control micro-milling, FIG. 1c, top; laser engraving; FIG. 6, top; anisotropic etching of silicon (Ungrin, M. D., et al. PLoS One 3, e1565 (2008)), FIG. 6 bottom), a bicycle reflector purchased in a neighborhood bicycle shop (FIG. 1c middle), and a commercially available pyramidal micro-well chip (Stem Cell Technologies; FIG. 5).

An ideal patterning technology would be adaptable and modular in nature in order to enable orthogonal combination with other patterning strategies. It was therefore tested whether this method is compatible with previous generation engineering technologies as well as multiple material systems. It was demonstrated that microorganized cell layers produced separately by substrate-based molding could be stacked manually for multilayer patterning (FIG. 1c bottom). In particular, it was shown that micro-organized cell layers produced separately by substrate-based molding retain the capability to be stacked manually for multi-layer patterning (FIG. 1c bottom). Importantly, cells in these patterns and throughout this paper were labeled using green and red calcein-AM dyes, which are retained only by living cells with intact plasma membranes. Red and green-colored cells in all images are therefore viable. These studies demonstrate the production of hydrogels containing viable cells arranged in a variety of multi-cellular patterns using MIRR molding.

Additionally, since InVERT molding segregates cellular patterning and encapsulation into distinct steps, this process permits cell encapsulation in a range of natural and synthetic materials with diverse properties, gelation triggers, tunability, and general availability and accessibility. The studies described above demonstrate the flexibility of this approach by encapsulating patterned cells in three different material systems: agarose (FIG. 1b middle), polyethylene glycol (FIG. 6 bottom), and fibrin (FIG. 1c top). Low melting point agarose, a common-place material in most biological laboratories, can be maintained as fluid at 37° C. after melting but cross-links via chain entanglement to form a large-pore macroreticular network upon cooling. Polyethylene glycol (PEG) is a highly-tunable synthetic system that can be covalently cross-linked by exposure to ultraviolet light. Fibrin is naturally derived, highly tunable, and polymerizes by the enzymatic cleavage of fibrinogen by thrombin. In these Examples, InVERT molding could be accomplished using fibrin (gelation by enzymatic polymerization with thrombin; FIG. 1c top), agarose (gelation by temperature-induced chain entanglements, FIG. 1c middle), and polyethylene glycol (gelation by external light-based photopolymerization; highly tunable; FIG. 6). The material in which cells are encapsulated determined pattern maintenance prior to cellular selforganization. For example, cells remain patterned for weeks without reorganization in nondegradable PEG gels but began to self-organize over the course of days in highly degradable, low concentration (e.g., 5 mg/ml) fibrin.

The time required to perform the InVERT molding inversion process was on the order of several minutes, and the timeframe for the entire process depended upon the polymerization time of the material. It was possible to produce six patterned hydrogels in 70 minutes using fibrin gel, 35 minutes using agarose, and 12 minutes using polyethylene glycol. Thus, at its best, this process produced micropatterned gels at a rate of two minutes per gel. Additionally, since InVERT molding required no equipment beyond the intaglio topographic substrate and a standard tissue culture centrifuge, parallel and scaled production in a variety of laboratory settings is possible. Together, these results illustrate the versatility of this method for performing rapid multi-compartmental cellular patterning in various orientations and material systems.

Figure 1D:
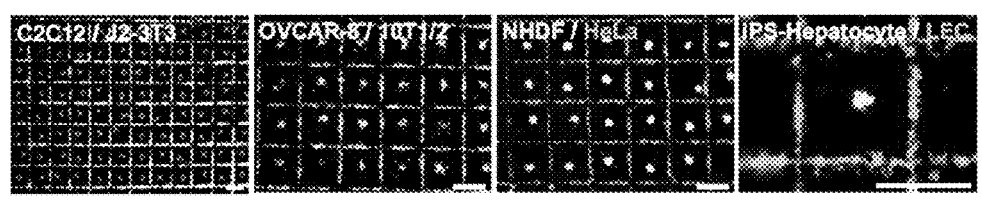
Figure 7:
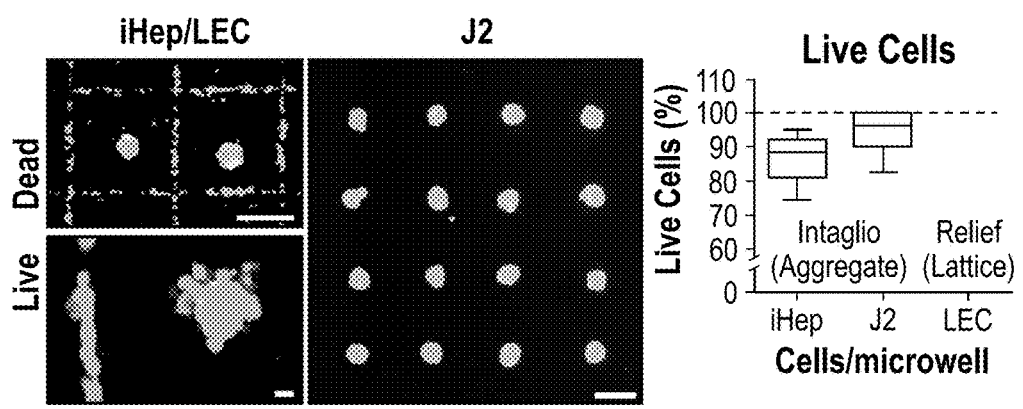
FIG. 7. Live/Dead Analysis of tissues patterned with InVERT molding. Representative images of tissues stained with calcein-AM (live cells, green) and ethidium homodimer (dead cells, red) demonstrate that most cells survived InVERT molding [left; iPSHeps (iHep) patterned in intaglio phase after pre-aggregation with liver endothelial cells (LEC) in the relief phase; center, J2 fibroblasts patterned in the intaglio phase after pre-aggregation]. Scale bar 200 μm for all images for low magnification and 20 μm for high magnification (lower left) images. Quantification of living cells demonstrated that survival was at worst 87±1% (iHep, S.E.M.) and at best 99±1% (LEC, S.E.M.). Box plot whiskers denote minimum to maximum values.

Finally, to illustrate the applicability of InVERT molding to numerous biological systems, multiple parenchymal cell types were patterned with a variety of non-parenchymal stromal or endothelial cell types. Since InVERT molding is based on cell sedimentation or centrifugation, this process is robust regardless of cell-specific physical properties that can impact cell patterning in other systems (e.g., size, density, charge). Multicellular model systems relevant for examining the role of stroma in muscle or cancer biology were created [FIG. 1d; mouse C2C12 skeletal myoblasts with mouse J2-3T3 fibroblasts, human ovarian carcinoma cells (OVCAR-8) with stromal mouse embryonic fibroblasts (10T1/2), and human cervical cancer cells (HeLa) with stromal normal human dermal fibroblasts (NHDF)]. Since InVERT molding does not exert forces on cells that would not otherwise be experienced during routine tissue culture, it was hypothesized that this technique would be extensible to 'sensitive' cell types that have not been not been patterned successfully using other, art-described methods (e.g., iPS-derived cells). Towards this end, InVERT molding was used to pattern human iPS-Heps with liver endothelial cells (TMNK1; LEC) (FIG. 1d). By visualizing molded cells in all panels of FIG. 1 with calcein viability dyes, it was observed that most cells examined retained intact plasma membranes (FIG. 1; all panels with fluorescently labeled cells). Quantitative live-dead analysis using calcein-AM (live, green) and ethidium homodimer (red) demonstrated that the percentage of living cells was cell-type dependent and reached 99±1% (S.E.M., FIG. 7). These results demonstrate that cells, despite physical properties or origin, can be patterned, encapsulated, and demolded using the InVERT molding technique. InVERT molding could thus be useful in a variety of biological model systems and engineered tissue applications.

Example 2

Figure 2B:
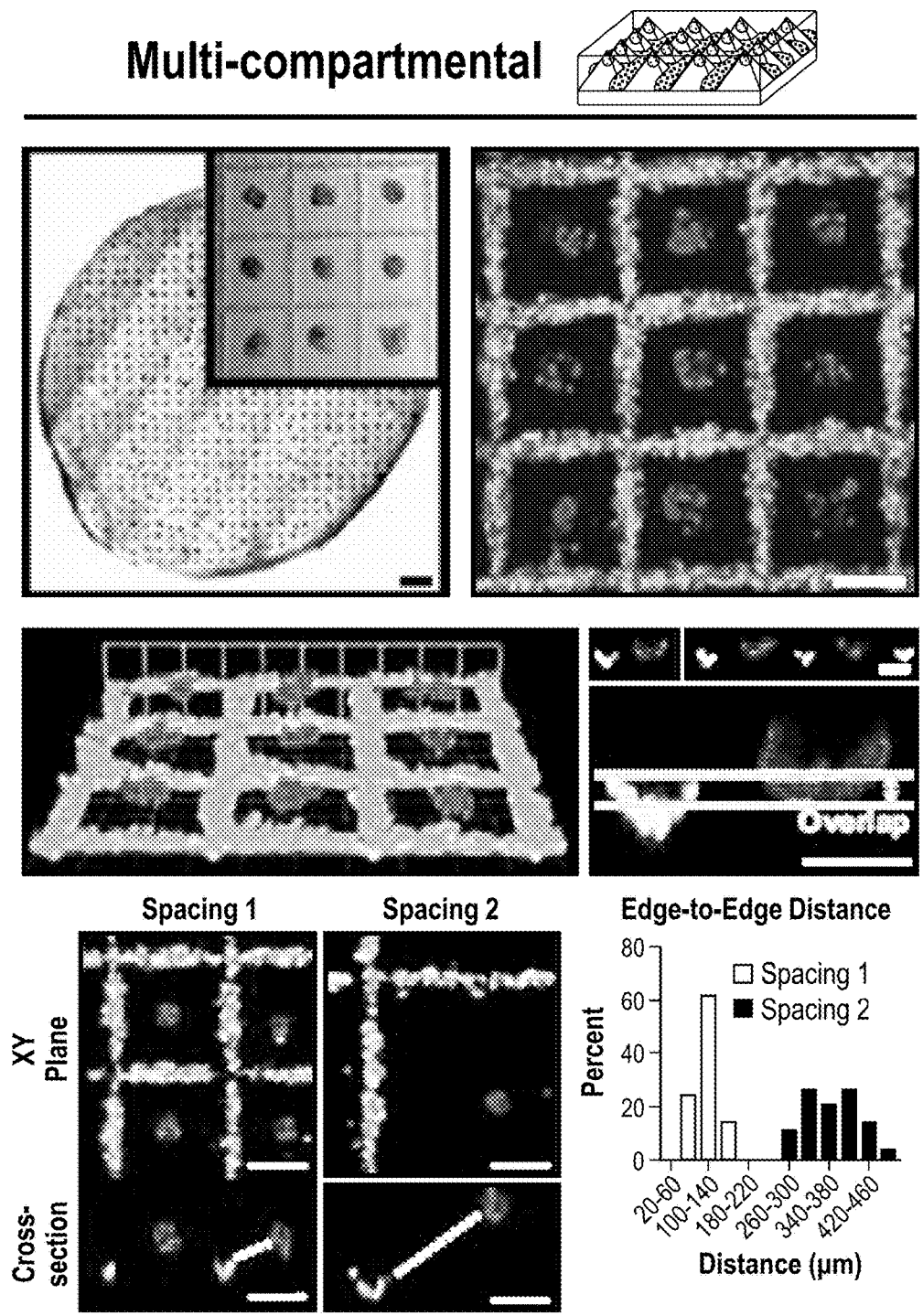
FIG. 2. Multi-cellular micro-organization can be controlled across distinct compartments. (a) For distinct multi-compartmental cellular patterning, hepatic aggregates (red) were embedded within an endothelial lattice (green) using InVERT molding. (b) Each hydrogel was 1.5 cm in diameter and contained approximately 1000 aggregates (representative phase images, left, scale bar 1 mm, inset 200 uM). Hepatic aggregates (red, calcein red-orange AM) were patterned with high spatial regularity within the endothelial lattice (green; calcein-AM, top right, scale bar 200 µM). Three dimensional cellular patterning is evident from opaque oblique and cross sectional rendering of stacked multiphoton images (middle; grid scale bar 127 µm). A single cross-section slice demonstrates that the two cellular compartments overlap in the same Z plane (blue lines) but are distinct and non-overlapping in the XY plane (middle right). Altering cell seeding density of 12 fibroblast aggregates and liver endothelial cells can eliminate overlap (bottom left; scale bars are 110 µm). Edge-to-edge distance (dotted white line) between cellular compartments followed distinct Poisson distributions for different spacings (bottom right). (c) An average of 10-500 hepatocytes were seeded per microwell. Resultant aggregates were either encapsulated in hydro gels or removed for immunostaining analysis. Aggregates encapsulated in hydrogels (left, scale bar 200 µm) exhibit Poisson distribution (center). Cytokeratin immunostaining of isolated aggregates reveals distinct morphology across aggregate sizes (right, scale bar 50 µm). (d) Multiphoton imaging of hydro gels with patterned aggregates containing both hepatocytes and 12 fibroblasts demonstrates that fibroblasts were dispersed throughout each hepatic aggregate (fibroblasts, mCherry; hepatocytes, calcein-AM, scale bar 50 µm). Representative aggregates show fibroblasts located at both the edges and center of the aggregates (bottom).

Characterization of Multi-Compartmental Cellular Microorganization; High-fidelity Microorganization of Multiple Cell Types Across Distinct Compartments Existing scalable technologies do not allow interrogation of the functional impact of placement of multiple compartments in engineered tissues on the parenchyma. Endothelial cells of the vasculature modulate parenchymal tissue functions in both health and disease (Ding, B. S. et al. *Nature* 468, 310-315 (2010); Ding, B. S. et al. *Cell* 147, 539-553 (2011); Franses, J. W., et al. *Sci Transl Med* 3, 66ra65 (2011); and Aird, W. C. *Pharmacol Rep* 60, 139-143 (2008)) and play an ultimately non-dispensable role in oxygen and nutrient delivery. It was therefore desired to demonstrate the power of the InVERT molding technique by controlling the micro-scale patterning of distinct 'parenchymal' and 'vascular' compartments in 3D engineered liver tissue. Primary rat hepatocytes were seeded in microwell patterning substrates, incubated overnight to enable the formation of cellular aggregates with intact intercellular contacts, and encapsulated patterned aggregates in a hydrogel. The InVERT molding platform was then used to encase micro-patterned hepatic aggregates (red; calcein red-orange AM) within a distinct endothelial cell lattice (green; calcein AM) in a single monolithic hydrogel without the need for layering or manual micromanipulations (FIGS. 2a and 2b top) Each hydrogel in these studies was 1.5 cm in diameter and contained approximately 1000 hepatic aggregates (FIG. 2b, top left; each aggregate composed of ~125 cells). Opaque oblique and cross-sectional renderings of stacked multiphoton images demonstrated that patterned cells have distinct cellular depth in the Z direction and that together the cellular compartments span approximately 130 µm in thickness (FIG. 2b middle). Importantly, hepatic and endothelial compartments exhibit substantial Z-plane overlap in this monolith gel system, which is not believed to be possible using any other 'top-down' 3D system (FIG. 2b middle). In essence, unlike systems that create multicellular patterning by stacking separate layers, hepatic and endothelial compartments exhibit substantial Z-plane overlap in the InVERT molded tissue (FIG. 2b, middle).

Further analysis of a single slice through the XZ plane demonstrated that the patterning of the two cellular compartments is indeed distinct and non-overlapping in the X-Y plane (FIG. 2b middle). Z-plane overlap can be reduced or removed by altering cell concentration in each compartment (FIG. 2b, bottom left). Different signaling activators and inhibitors are known to act across varying distances, but relative contributions of specific factors responsible for such differences have not been elucidated due to in vivo model system complexity (Muller, P., et al. Dev Cell 21, 145-158 (2011); Hamada, H., Dev Cell 22, 911-912 (2012); and Muller, P., et al. Science 336, 721-724 (2012)). A 3D system that precisely places two cell populations at varying distances could enable previously impossible in vitro interrogation of distance-reliant multicellular interactions. Here, edge-to-edge spacing between tissue compartments was controlled by altering the topography of the intaglio patterning substrate used for InVERT molding (FIG. 2b, bottom left). Average edge-to-edge distances were 116±2 µm and 366±4 µm ($p<0.01$, S.E.M.), which are also relevant for studying intercellular communication via soluble signals (Muller, P., et al. Dev Cell 21, 145-158 (2011) and (Hui, E. et al *Proc Natl Acad Sci USA* 104, 5722-5726 (2007)). Together, these results demonstrate the ability to control inter-compartmental spacing and microorganization of multiple cell types across distinct tissue compartments using InVERT molding. In particular, these results demonstrate high-fidelity micro-organization of multiple cell types across two distinct 'parenchymal' and 'vascular' engineered tissue compartments.

Example 3

Figure 2C:
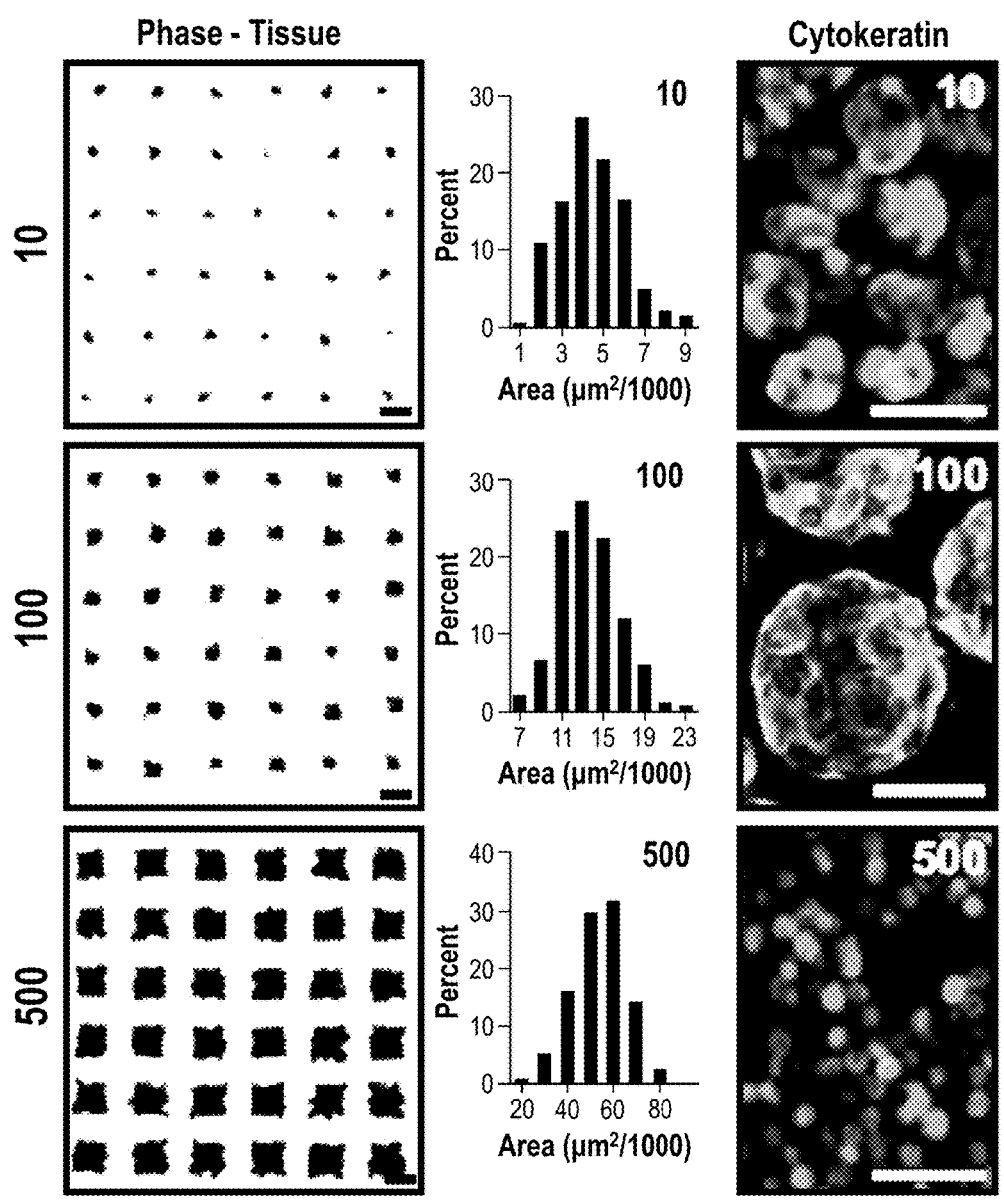
Figure 2D:
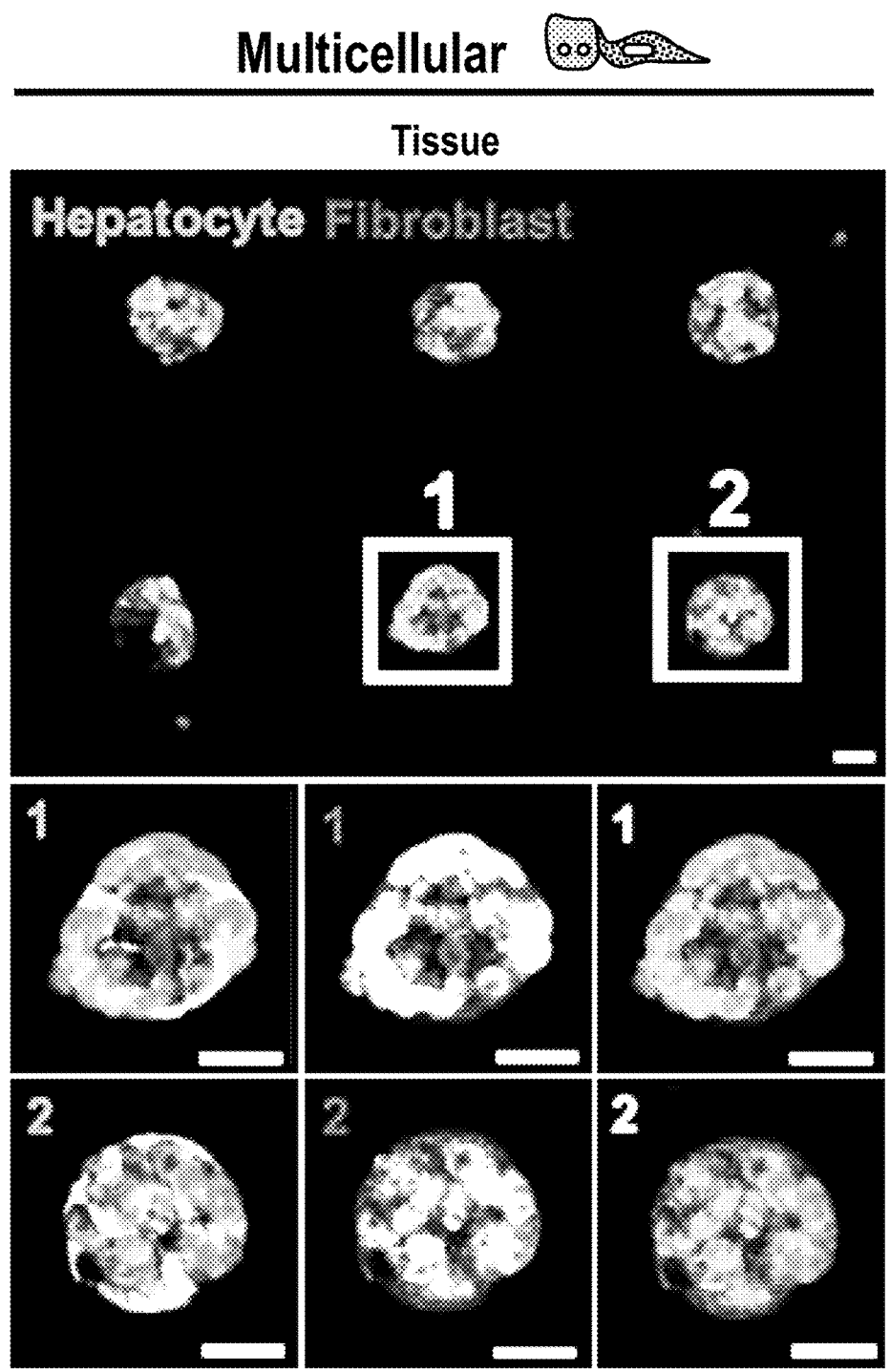

Hierarchical Modulation of Microstructure and Multi-cellular Composition within a Given Compartment Complex tissues are hierarchically organized across multiple length-scales and contain numerous cell types. In particular, such complex tissues are hierarchically organized such that each tissue compartment is further organized at both the microstructural and multicellular level. Thus, it was next examined whether additionally fine-tuning of the microstructure and multi-cellular composition within a tissue given compartment could be accomplished using InVERT molding. Specifically, we refined the hepatic compartment produced during the initial Intaglio-Void-Embed portion of the InVERT molding protocol without adding a second cell population ('relief' phase). To test whether the microstructure of aggregates in the hepatic compartment could be reproducibly modulated, primary rat hepatocytes were seeded in microwell patterning substrates at densities of 10-500 cells per microwell, incubated cells overnight, encapsulated patterned aggregates in a hydrogel, and then imaged and quantified resultant microstructures using the automated platform described herein (FIG. 2c-d). Cell seeding into the patterning substrate was based on cellular sedimentation, and therefore the combined use of oblique microwell side-walls and complete surface tiling resulted in collection of all cells within a defined volume.

It was found that variation in hepatocyte seeding density from 10-500 cells per microwell produced distinct Poisson distributions of aggregate size (FIG. 2c). Aggregates formed from 10, 100, and 500 cells per microwell had average diameter of $50\pm1\times10^2$ µm$^2$, $145\pm2\times10^2$ µm$^2$, and $590\pm5\times10^2$ µm$^2$, respectively. Immunohistological analysis of hepatocyte aggregates demonstrated that aggregates of different sizes exhibited distinctly different morphologies. Specifically, aggregates created from 10 or 100 hepatocytes per microwell contained intact intercellular junctions, whereas cells in larger aggregates remained isolated and dispersed (FIG. 2c, right; cytokeratin, green; note scale bar is 50 µm for all histological images). To test the ability to additionally modulate multi-cellular composition in a given micro-patterned cellular compartment, mural J2 fibroblasts ('fibroblasts'), which have been shown previously to stabilize hepatic functions, were homogeneously mixed with hepatocytes during cell seeding of microwells and encapsulated the resultant aggregates in hydrogel. This resulted in the formation of hydrogels containing 'hetero-aggregates' composed of both hepatocytes and fibroblasts (FIG. 2d.). Multiphoton imaging of hydrogels containing micropatterned hepatocyte/fibroblast aggregates demonstrated that fibroblasts expressing mCherry (red) were intercalated throughout the hepatic spheroids (hepatocytes green, calcein-AM) in our system (FIG. 3d). Taken together, these results demonstrate our ability to hierarchically modulate both microstructure and multi-cellular composition within a given tissue compartment using InVERT molding.

Example 4

Figure 3A:
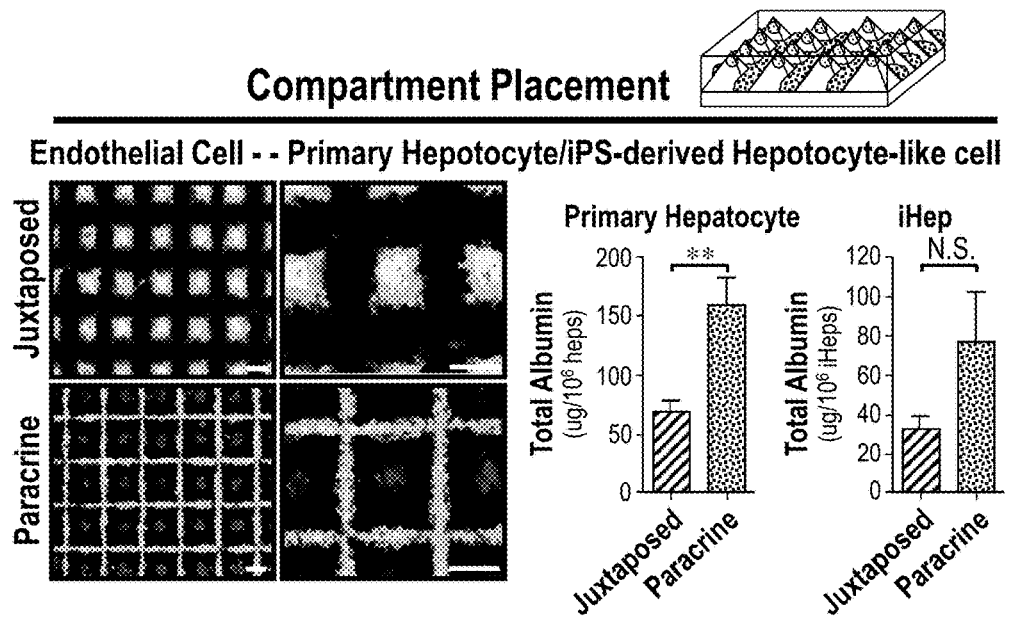
FIG. 3. Multi-level structural optimization or multi-compartmental placement dictates hepatic tissue function. (A) To test whether multi-compartmental placement modulates tissue function, liver sinusoidal endothelial cells (green) were patterned either directly juxtaposed with hepatocyte/fibroblast aggregates (red) or in a compartmentally distinct cellular lattice (paracrine conformation) (scale bar 200 µm). Lattice conformation resulted in enhanced albumin secretion compared to juxtaposed patterning both over time (left) and cumulative (right). Paracrine configurations for primary hepatic aggregates and liver endothelial cells yield significantly greater albumin secretion than juxtaposed configurations ($P=0.0087$, $n=5$ and $6$ for each respective group, Mann Whitney test), and similar trends were observed for iPS-Hep aggregates though this data was not significant ($P=0.3500$, $n=3$ for both groups, Mann Whitney test) (b) Stromal cells (green) were patterned either in paracrine, juxtaposed' or 'interpenetrating' conformation relative to iPS-hepatocyte-like cells using InVERT molding (scale bars 200 µm). Interpenetrating configurations yield higher albumin secretion relative to other conformations ($P=0.0250$, $n=5, 4, 6, 6$ for each respective group; One-way ANOVA with Tukey post-hoc test).
Figure 8:
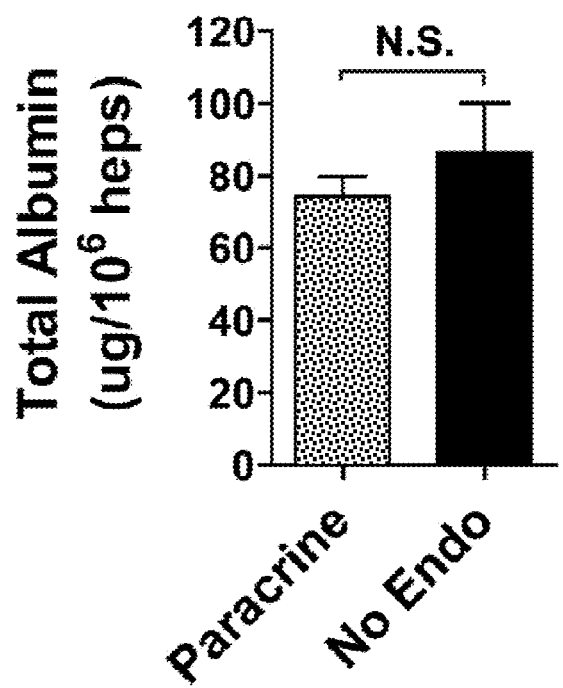
FIG. 8. Inclusion of endothelial cells in hepatic tissues. Liver sinusoidal endothelial cells (green) were patterned in compartmentally distinct 'paracrine' conformation relative to hepatic aggregates using InVERT molding or not included in tissues ('No endo'—hepatic aggregates only). Albumin secretion was not statistically different between conditions (P=0.5887, n=6 for each group, Mann Whitney test).

Probing the Effect of Compartmental Placement on Tissue Function; Microorganization of Endothelial Compartment Influences Parenchymal Tissue Function Multi-cellular tissue architecture defines the cell-cell contacts and paracrine signaling gradients that ultimately determine tissue function. It was therefore hypothesized that the placement of distinct cellular compartments as well as micro-organization and cellular composition within compartments would dictate physiologic tissue function of engineered liver tissue in vitro. This Example demonstrates the biological applicability of InVERT molding. It was first tested whether placement and organization of the vascular compartment modulates hepatic parenchymal tissue function in the engineered tissue system, since endothelial cells can modulate parenchymal functions in both health and disease via the release of 'angiocrine' factors (Ding, B. S., et al. Nature 468, 310-315 (2010) and Franses, J. W., et al. Sci Transl Med 3, 66ra65 (2011)). Liver sinusoidal endothelial cells (green) were patterned either directly into microwells with (adjacent to) hepatocyte/fibroblast aggregates (red) prior to hydrogel encapsulation ('juxtaposed conformation') or in a compartmentally distinct cellular lattice ('paracrine conformation') via InVERT molding (FIG. 3a). Total hepatocyte, fibroblast, and endothelial cell numbers were held constant in all hydrogels. The results indicated that patterning endothelial cells in a distinct lattice ('paracrine conformation') significantly enhanced albumin secretion, a surrogate measure of hepatic function, over 2-fold compared to patterning endothelial cells juxtaposed to hepatic aggregates ($*p<0.05$) (FIG. 3a). Hepatic aggregates patterned without endothelial cells exhibited similar functional activity to those patterned in 'paracrine' conformation (FIG. 8). This finding demonstrates that endothelial stabilization of hepatic phenotype is dependent upon microorganization of the vascular compartment. In essence, these findings demonstrate that varying the microorganization of the endothelial compartment can alter the hepatic functions of engineered tissues.

Example 5

Figure 3B:
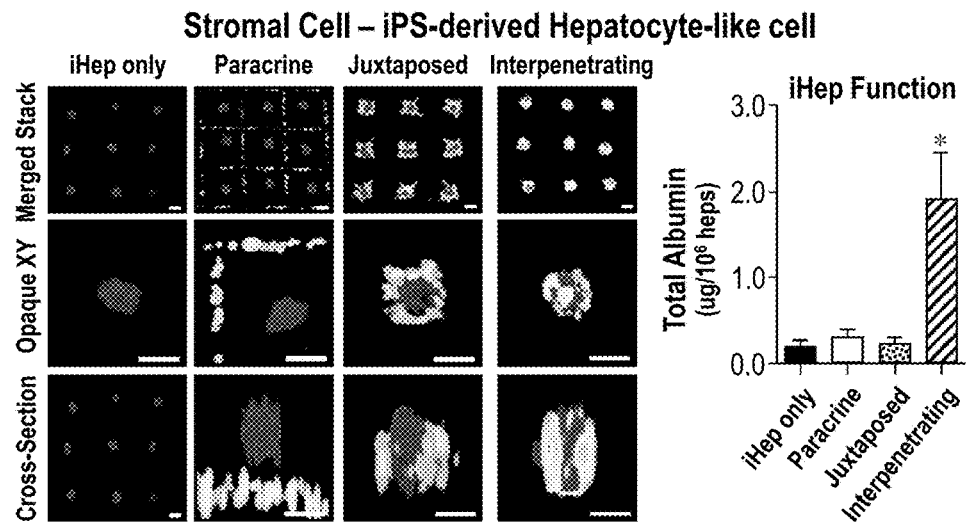

Microorganization of Stromal Compartment Modulates iPS-hepatocyte-like Cell Function Human iPS cells have potential for use in in vitro model systems as well as translatable human cell-based tissue therapies. In the context of the liver, human hepatocyte-like cells have recently been generated from iPS and used in 2D model systems (Schwartz, R. E., et al. Proc Natl Acad Sci USA 109, 2544-2548 (2012) and Si-Tayeb, K., et al. Hepatology 51, 297-305 (2010)), but optimal architectural parameters for organizing these cells in a 3D setting have not been elucidated. It was thus sought to use InVERT molding to dissect multicellular geometrical conformations necessary for the maintenance of hepatic iPS-Hep function. It was first tested whether patterning of liver sinusoidal endothelial cells in juxtaposed or paracrine conformation modulates iPS-Hep function and it was found that, similar to primary hepatocytes, patterning in paracrine conformation trended towards enhanced hepatic function, though these results were not significant. Next, iPS-Heps (red) were seeded at a density of 100 cells per microwell, and stromal fibroblasts (green; constant number for all hydrogels) were patterned in a compartmentally distinct lattice ('paracrine' conformation'), adjacent to iPS-Hep aggregates that had already compacted ('juxtaposed' conformation), or directly into microwells with iPS-Heps to create a heteroaggregate ('interpenetrating' conformation) (FIG. 3b). Direct patterning of stromal cells to form heteroaggregates (interpenetrating') resulted in optimal hepatic function (FIG. 3b), suggesting that local paracrine or direct contact signals with the stroma are important for the function or maturation of iPS-Heps (FIG. 3b).

Example 6

Figure 4A:
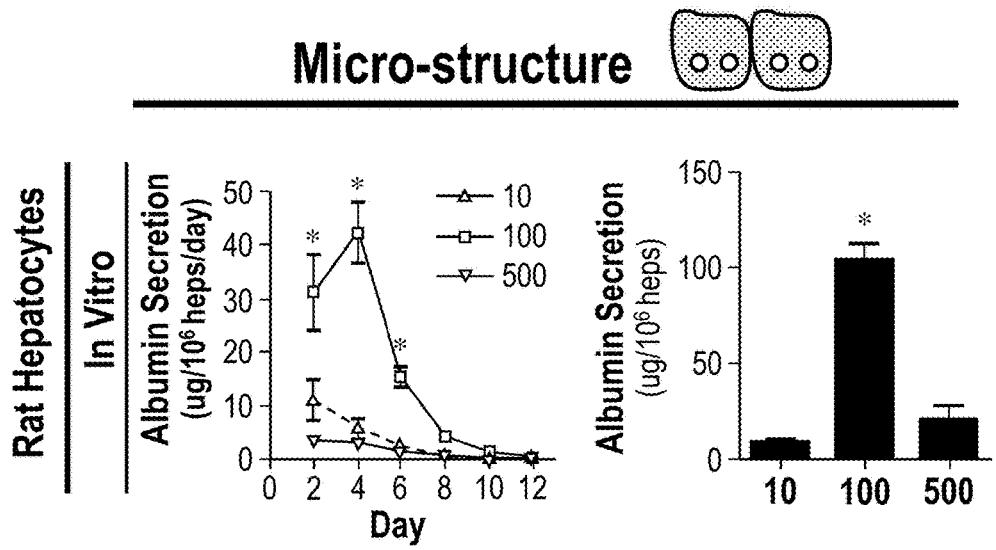
FIG. 4. Architectural optimization of engineered hepatic tissue controls function in vitro and dictates survival and function after implantation. Optimization of engineered hepatic tissue architecture controls function both in vitro and after implantation. (a) The number of hepatocytes per aggregate (10-500) resulted in distinct hepatic tissue function in vitro (*$p<0.05$, SEM, $n=4, 3, 3$, for each respective group, Kruskal-Wallace test). (b) Addition of J2 fibroblasts to hepatic aggregates in hydrogels sustained (left) and improved cumulative (right) hepatic functions in a dose-dependent manner in vitro (100 hepatocytes per aggregate + fibroblasts at 1:0, 1:1, 1:2 hepatocytes:fibroblast, *$p<0.05$, SEM, $n=5, 5, 4$ for each respective group, One-way ANOVA with Tukey post-hoc test). (c) Representative bioluminescence images of nude mice that received patterned tissue containing no cells ("Blank"), 500 rat primary hepatocytes per aggregate ("500"), 100 hepatocytes per aggregate ("100"), or 100 hepatocytes + J2 fibroblasts per aggregate ("100+J2") implanted in the intra-peritoneal space. (d) Optimal in vitro tissue configurations result in sustained hepatic functions to over four weeks following implantation (*p<0.05, SEM, n=3, 4, 5, 6 for each respective group, Kruskal-Wallace test with Dunn's Multiple Comparison post-hoc test). (e) Representative histological images of patterned tissues containing 100 crypreserved human hepatocytes per aggregate with or without J2 fibroblasts ("100" or "100+J2") that were extracted seven days after intra-peritoneal implantation in nude mice. Patterned arrays of aggregates (left, hematoxylin and eosin) that contained arginase-1 positive hepatocytes (right, ARG-1, red) were identified in all animals with cellular implants (scale bars 100 μm). (f) The addition of fibroblasts sustained human hepatic function for at least four weeks (*p<0.05, n=4, 6, 6 for each respective group, Mann-Whitney test, 'blank' excluded from statistical analysis).
Figure 4B:
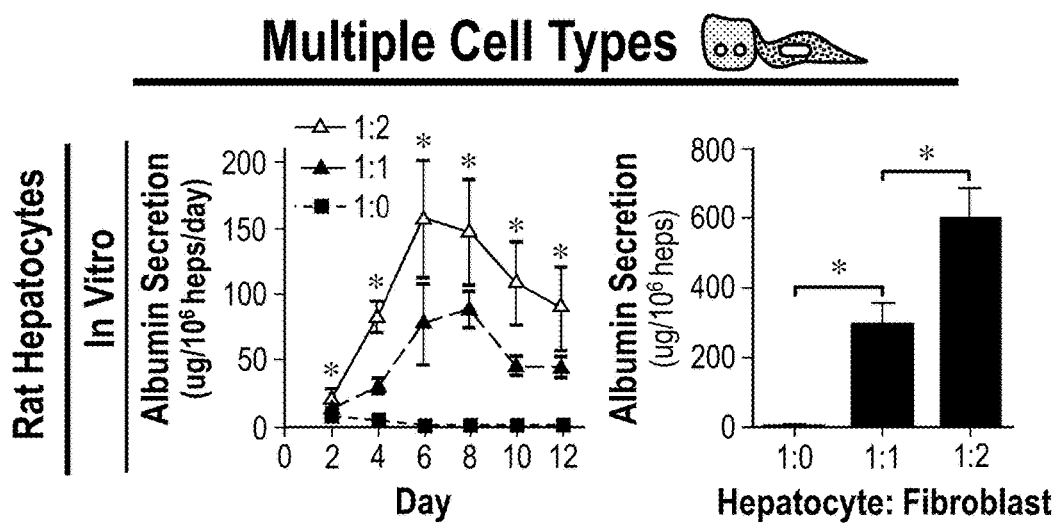

Probing the Effect of Microstructural and Multi-cellular Optimization within a Compartment on Tissue Function It was next tested whether further alternations in the microstructure and multi-cellular composition of aggregates in the parenchymal compartment impacts engineered liver tissue function. To alter parenchymal compartment microstructure, hydrogels were created containing 10, 100, or 500 hepatocytes per homotypic aggregate. Hepatic albumin secretion was highly dependent on the number of hepatocytes plated per microwell (FIG. 4a). Indeed, tissues containing 100 hepatocytes per aggregate produced 14-fold greater albumin compared to tissues containing 500 hepatocytes per aggregate after 4 days in culture (FIG. 3a). These results were notable given the morphological differences between aggregates containing 100 or 500 hepatocytes (FIG. 2c). Hepatic functions declined with time in hydrogels containing only hepatocytes in all studies in which aggregates were composed only of hepatocytes (FIG. 4a, left). It was hypothesized that additional control of multi-cellular composition within the parenchymal compartment would further stabilize tissue function, as had been shown previously in other model systems. The addition of fibroblasts in patterned tissues, i.e., the inclusion of hepatocyte-fibroblast heteroaggregates in patterned tissues, resulted in enhanced and prolonged hepatic functions to at least 12 days in a dose dependent manner (FIG. 4b, right). These results demonstrated that, in addition to compartmental location, further modulation of both microstructure and multi-cellular composition of the units within a given compartment (here the parenchymal compartment) impacts engineered tissue function. These results demonstrated that, in addition to relative compartmental location, the microstructure and multicellular composition of the units within a given compartment (here, the parenchymal compartment) significantly impacts engineered tissue function. Together, these results demonstrate the biological importance of multi-level or hierarchical architectural optimization when constructing engineered tissues.

Example 7

Figure 4C:
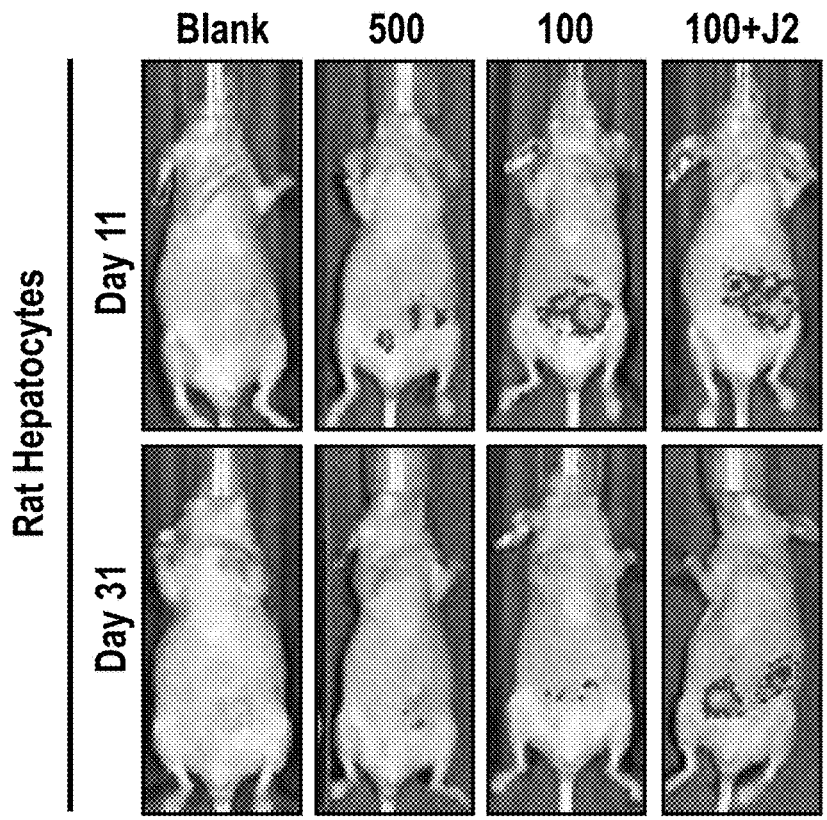
Figure 4D:
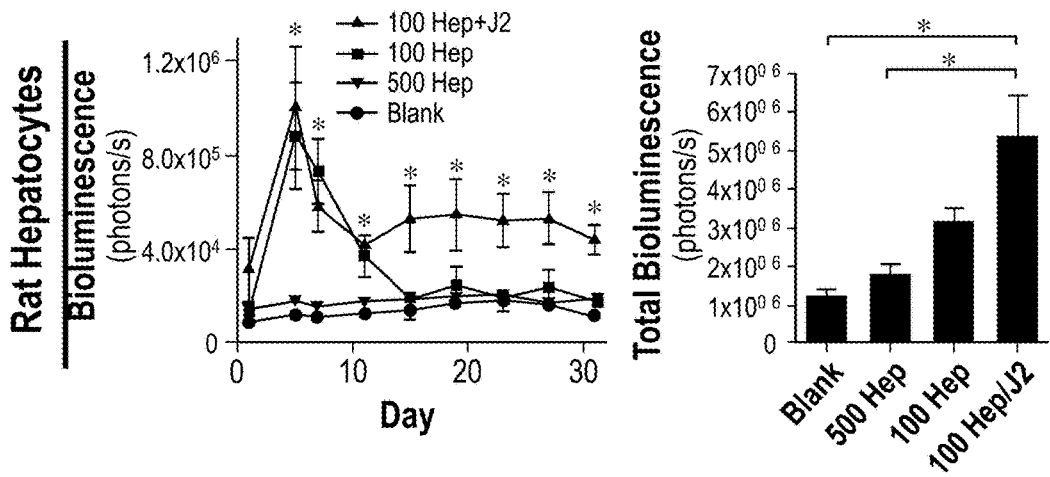

Multi-cellular Micro-organization Prior to Implantation Impacts Hepatic Survival and Function in vivo Successful clinical translation of complex engineered tissue requires the maintenance of highly functional parenchyma following tissue implantation. It was hypothesized that the architectural conformations that resulted in optimal tissue function in vitro would also prove optimal after in vivo tissue implantation. To test this hypothesis, primary rat hepatocytes were transduced with a lentivirus in which a modified albumin promoter (Chen, A. A., et al. *Proc Natl Acad Sci USA* 108, 11842-11847 (2011)) drives the expression of firefly luciferase. It had been previously demonstrated that luciferase activity is directly proportional to albumin secretion in vitro in this system. Patterned engineered liver tissues were created according to the specifications that produced differing hepatic functions in our in vitro studies (i.e., 100 vs. 500 hepatocytes per aggregate and +/− fibroblast inaggregates with 100 hepatocytes), and the resulting tissues were implanted in the intraperitoneal (IP) space of nude mice, and monitored bioluminescence of the grafted tissues. Parallel to the above-described in vitro observations, the number of hepatocytes per aggregrate dramatically affected tissue survival and function, i.e., the number of hepatocytes per aggregate augmented tissue function over 4-fold by five days after implantation, and was optimal at 100 hepatocytes per aggregate (FIG. 4c-d). The addition of fibroblasts enhanced hepatic function 2-3 fold starting at day 15 and maintained albumin secretion for at least four weeks post-implantation (FIG. 4d). Hepatic survival and function declined rapidly in hydrogels containing only hepatocytes. J2 fibroblasts were thus included in hepatocyte aggregates and it was found that the addition of fibroblasts prolonged hepatic function after implantation by several weeks (FIG. 4c-d). Thus, cellular architectures found to be optimal through in vitro experimentation also resulted in superior tissue survival and physiologic function after transplantation into nude mice. These studies demonstrate the importance of optimizing engineered tissue architecture for maximal survival and function following implantation.

Example 8

Implantation of Human Hepatic Tissues

Figure 4E:
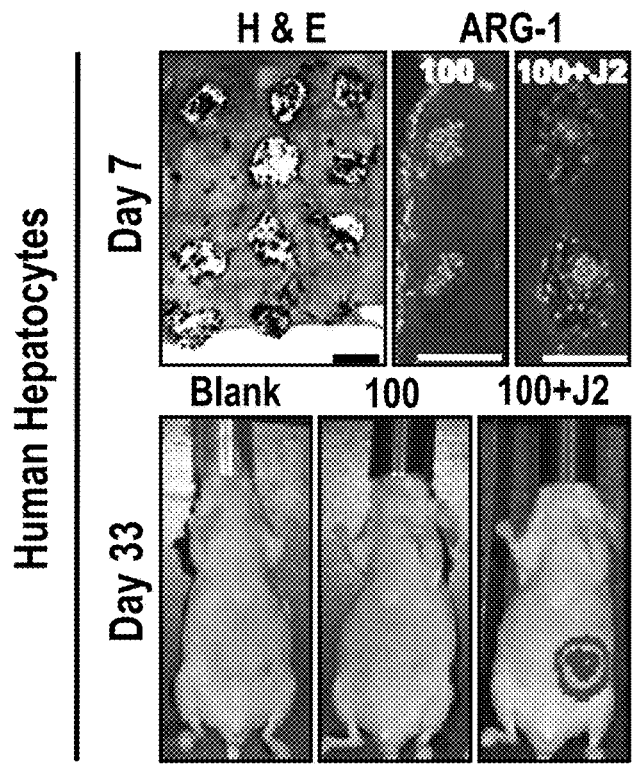
Figure 4F:
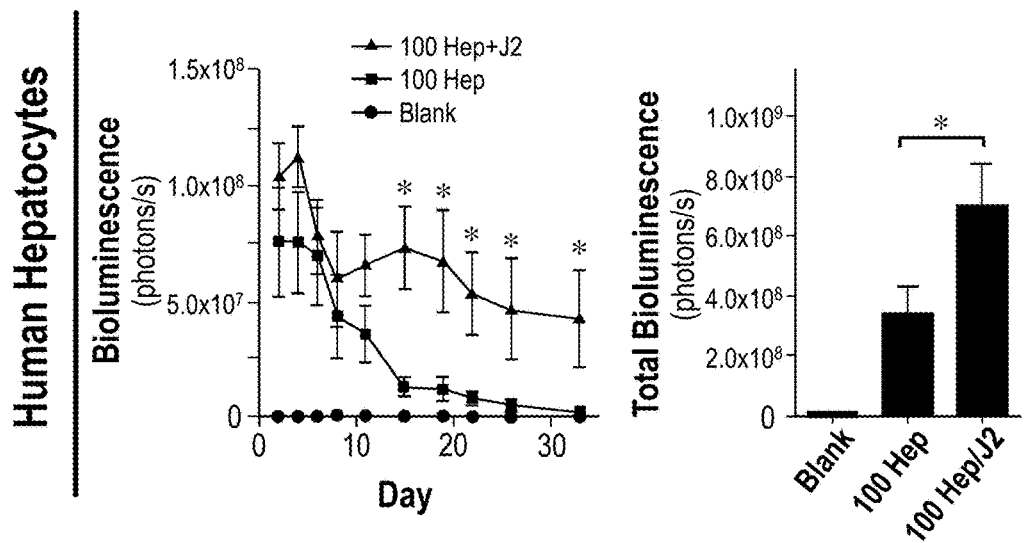
Figure 9:
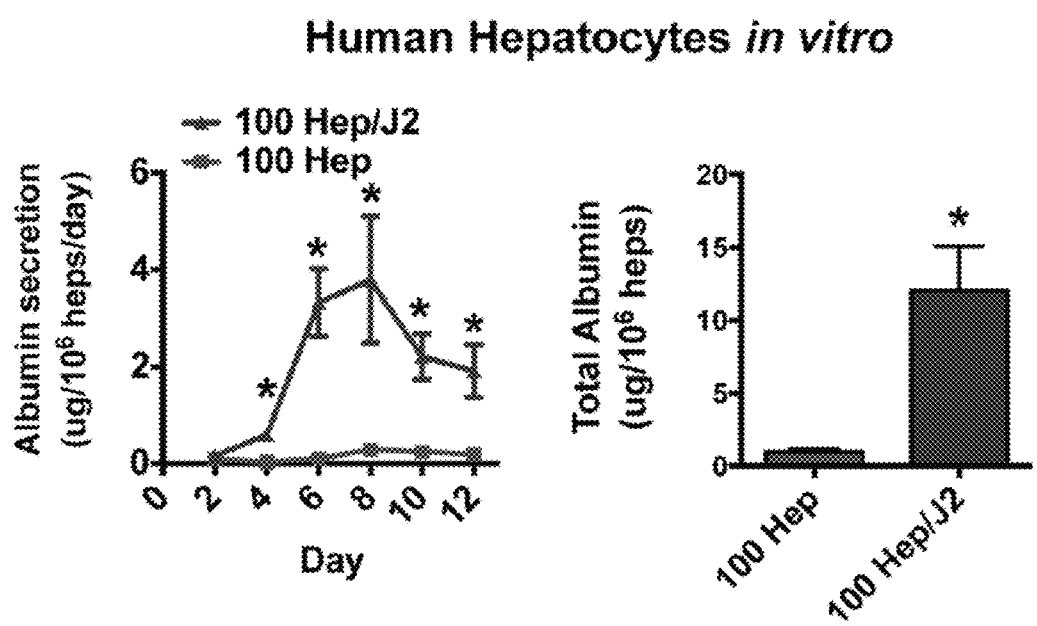
FIG. 9. Function of patterned hepatic tissues containing human hepatocytes is improved significantly by the addition of J2 fibroblasts to aggregates (time course, left; cumulative albumin, right; *p<0.05, SEM, n=5, 6 for each respective group).
Figure 10:
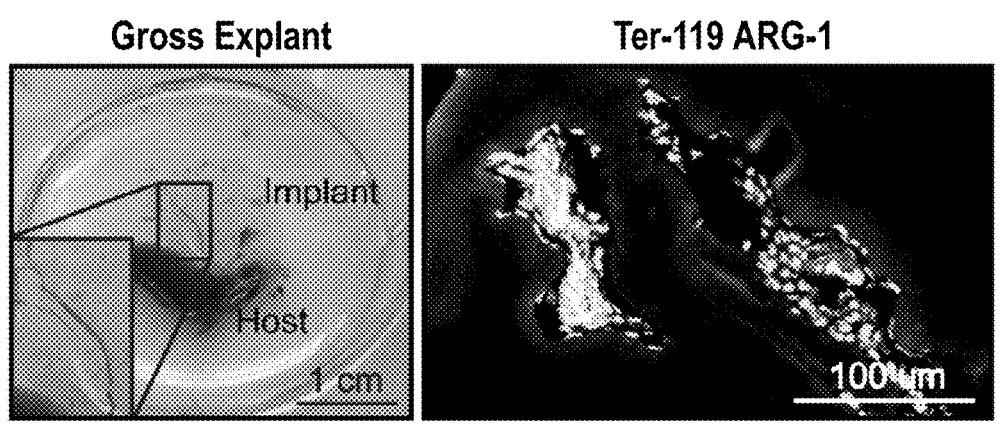
FIG. 10. Cryopreserved human hepatocytes expressing luciferase under the control of a modified albumin promoter were patterned in tissues with 100 hepatocytes +/− fibroblasts and implanted in the IP space of nude mice. A representative tissue upon resection of engineered tissues at day 7 demonstrates adhesion to host tissue and the presence of bloodcarrying vessels. Ter-119 positive red blood cells (green) were identified in these explants near but not typically immediately juxtaposed to arginase-1 (ARG-1, red) positive hepatocytes (right).

It was hypothesized that since the InVERT methods of the invention provide for patterning of delicate cell types, patterned tissues containing clinically relevant, cryopreserved human hepatocytes would survive and function in vitro and in vivo. It was found that, similar to tissues containing rat hepatocytes, tissues with human hepatocytes that contained fibroblasts exhibited secreted over 33-fold greater albumin by day 6 days compared to those containing only hepatocytes in vitro (FIG. 9). Human hepatocytes expressing luciferase under the control of a modified albumin promoter were then patterned in tissues that contained heteroaggregates of 100 hepatocytes +/− fibroblasts, and implanted in the IP space of nude mice. Histological examination of explanted human hepatocyte tissues demonstrated that patterned arrays of hepatic aggregates were generally retained at one week post-implantation (FIG. 4e, left, hematoxylin and eosin). Arginase-1 (ARG-1) immunostaining identified human hepatocytes within the aggregates, which self-sorted to the center of each aggregate in tissues that contained fibroblasts by one week post-implantation (FIG. 4e, right). Gross examination upon resection of engineered tissues at day 7 demonstrated that 74% of implants adhered to host tissue (14 of 19 tissues, FIG. 10), and Ter-119 positive red blood cells were identified in these explants. The average distance from Ter-119 positive blood and the nearest ARG-1 positive-hepatic aggregate was 119±32 µm (S.E.M.; FIG. 10), suggesting that nutrient transport in the system occurred via diffusion from de novo vessels derived from the host to the hepatic aggregates. Similar to rat hepatic tissues, hepatic function in aggregates with 100 hepatocytes was sustained by the presence of fibroblasts (FIG. 4f). Thus, optimal cellular architectures that sustained hepatic functions in vitro to day 12 also resulted in superior physiologic tissue function for at least four weeks after transplantation in preclinical animal models.

The above examples demonstrates that precise optimization of parenchymal and vascular compartments alters hepatic functions of engineered liver tissue. A critical challenge in engineering complex tissues is to develop systems that enable the incorporation of multiple tissue sub-compartments. As one example, inclusion of a robust vascular compartment will ultimately dictate the survival, integration, and functional capacity of highly metabolic tissues such as the liver (Ennett, A. B. & Mooney, D. J. *Expert Opin Biol Ther* 2, 805-818 (2002) and Lee, H. et al. *Transplantation* 73, 1589-1593 (2002)) Indeed, recent studies have shown that establishment of an in vitro vascular network prior to implantation (i.e., 'pre-vascularization') greatly enhances the survival of the implant (Levenberg, S. et al. Engineering vascularized skeletal muscle tissue. *Nat Biotechnol* 23, 879-884 (2005) and Stevens, K. R. et al. Physiological function and transplantation of scaffold-free and vascularized human cardiac muscle tissue. *Proc Natl Acad Sci USA* 106, 16568-16573 (2009)).

In these studies, 'pre-vascularization' was achieved through endothelial selforganization and morphogenesis, and the end goal was to facilitate improved nutrient exchange to the grafted tissue upon implantation. In addition to their role in gas and nutrient exchange, endothelial cells comprising the vasculature play important roles in tissue development, homeostasis, and function. For example, endothelial cells are required for tissue development (Lammert, E., et al. *Mech Dev* 120, 59-64 (2003) and Matsumoto, K., et al. *Science* 294, 559-563 (2001)) even in the absence of blood flow (Cleaver, O. & Melton, D. A. *Nat Med* 9, 661-668 ((2003) and Lammert, E., et al. Science 294, 564-567 (2001)). They have also been shown to initiate and sustain liver regeneration (Ding, B. S. et al. Inductive angiocrine signals from sinusoidal endothelium are required for liver regeneration. *Nature* 468, 310-315 (2010)) as well as modulate other phenotypic states in health and disease (Ding, B. S. et al. *Cell* 147, 539-553 (2011); Franses, J. W., et al. *Sci Transl Med* 3, 66ra65 (2011) and Aird, W. C. *Pharmacol Rep* 60, 139-143 (2008)) through the release of 'angiocrine' factors. Previous two-dimensional studies have shown that hepatocyte and liver endothelial cell interactions can occur via paracrine interactions of at least 80 µm distance (March, S., et al. *Hepatology* 50, 920-928 (2009)). Here, it is shown that the simple presence of endothelial cells in 3D tissues is not sufficient to provide the optimal cues for controlling hepatocyte function. Rather, the structural organization of these cells dictates the degree of function and stabilization of the hepatic parenchyma. Specifically, organization in a lattice structure at approximately a 90 µm distance from cellular aggregates resulted in optimal hepatic function in this study.

The above examples next demonstrate that structural refinement of engineered tissues must be performed not only between but also within tissue compartments. In this study, it is shown that further optimization of the 3D parenchymal hepatic compartment, here composed of hepatic aggregates, or 'spheroids', altered tissue function. It was shown previously that encapsulation of primary hepatocytes distributed homogeneously in 3D engineered tissues immediately following isolation resulted in hepatocyte death (Underhill, G. H., et al. *Biomaterials* 28, 256-270 (2007)). It was reasoned that anoikis contributed to cell death and that microstructural control of intercellular contacts might improve hepatic function. Numerous techniques have been developed to create hepatic spheroids, which are known to have structural polarity, functional bile canaliculi, and hepatic functions (Abu-Absi, S. F., et al. *Exp Cell Res* 274, 56-67 (2002); Brophy, C. M. et al. *Hepatology* 49, 578-586 (2009); Glicklis, R., et al. *Biotechnol Bioeng* 67, 344-353 (2000); Landry, J., et al. *J Cell Biol* 101, 914-923 (1985); Lu, H. F. et al. *Acta Biomater* 1, 399-410 (2005); Moscona, A. *Exp Cell Res* 22, 455-475 (1961); Peshwa, M. V., et al. *In Vitro Cell Dev Biol Anim* 32, 197-203 (1996); Sakai, Y., et al. *Cell Transplant* 8, 531-541 (1999); Williams, C. M., et al. *Tissue Eng Part A* 17, 1055-1068 (2011); Nahmias, Y., et al. *Adv Biochem Eng Biotechnol* 103, 309-329 (2007); and Wong, S. F., et al. *Biomaterials* 32, 8087-8096 (2011)). However, these methods generate spheroids in which only 56-84% of total inoculated hepatocytes incorporate into spheroids after two days in culture, diameters of these spheroids range widely from 40-200 µm, and spheroids fuse and are lost with cell feeding over the course of culture time (Brophy, C. M. et al. *Hepatology* 49, 578-586 (2009)). The pyramidal microwell-based patterning system described here improves cell capture efficiency due to lack of dead space between microwells, allows precise control of cell number seeded per microwell and resultant aggregate diameter, and prevents aggregate fusion and loss over the course of time in culture by capturing aggregates at defined locations in 3D gels. In the instant studies, engineered tissues containing hepatic aggregates comprised of 100 hepatocytes (average edge-to-edge size of 135±1 µm) exhibited maximal albumin secretion. This agrees with results from a previous study, in which albumin secretion was found to be maximal at 100 µm diameter spheroid size[28]. Similar to previous studies, these functions were best sustained when aggregates also contained non-parenchymal J2 fibroblast (Lu, H. F. et al. *Acta Biomater* 1, 399-410 (2005) and Khetani, S. R. & Bhatia, S. N. *Nat Biotechnol* 26, 120-126 (2008)).

Finally, it is shown here that optimization of engineered hepatic tissue architecture dictates tissue survival and function after implantation into rodents. While several recent studies have shown that the inclusion of multiple cell types in engineered tissues can improve tissue survival and function following engraftment, and one study suggests that microvascular patterning can improve heart function after engraftment (Levenberg, S. et al. *Nat Biotechnol* 23, 879-884 (2005); Stevens, K. R. et al. *Proc Natl Acad Sci USA* 106, 16568-16573 (2009); Chen, A. A. et al. *Proc Natl Acad Sci USA* 108, 11842-11847 (2011); and Gaebel, R., et al. *Biomaterials* 32, 9218-9230 (2011)), the instant studies are believed to be the first to demonstrate the importance of optimizing multi-cellular tissue structure, e.g., parenchymal structure, prior to implantation to maximize tissue function post-transplant. It is herein demonstrated the utility of this technique for patterning and implanting tissues containing clinically relevant cryopreserved human hepatocytes. For ultimate application in clinical therapy, several additional advances might include the following. Z direction thickness of the InVERT molded tissue is currently limited by nutrient diffusion since patterned tissues do not contain conduits for fluid flow in vitro, and upon implantation the tissues examined here relied on vascularization by the host. Combination of the InVERT system with other technologies aimed at improving graft vascularization (Miller, J. S., et al. *Nat Mater* 11, 768-774 (2012) and Raghavan, S., et al. *Tissue Eng Part A* 16, 2255-2263, (2010)) could enable further Z direction patterning (and therefore increased tissue mass) and improved survival and function of metabolically-active hepatocytes. Additionally, it is proposed to be possible to demonstrate long-term survival of grafted cells and rescue of missing liver functions in genetic liver disease or acute liver failure model systems.

This platform technology, i.e., the InVERT molding platform described herein, will likely impact the creation of model systems for studying basic biology as well as lead to the development of specific architectural 'design specifications' for building engineered tissues, e.g., clinically-relevant engineered tissues, with optimal function in vitro and after implantation. This technology could be useful in diverse therapeutic fields ranging from regenerative medicine to cancer pathogenesis.

Methods

Microfabrication of Intaglio Patterning Substrates

PDMS templates of square pyramidal micro-wells and channels were fabricated as described previously (Ungrin, M. D., et al. *PLoS One* 3, e1565 (2008)) or purchased (Aggrewell, Stem Cell Technologies; 400 or 800 µm sidewall dimension of each square pyramidal micro-well). For micro-wells, wafers of 1-0-0 crystalline silicon were coated with silicon nitride. The silicon nitride was then selectively removed where the micropatterns were to be formed (e.g., microwells or branching structure) and the wafer was anisotropically etched to generate arrays of square-pyramidal wells. Following removal of the remaining silicon nitride layer, the wafer was used as a template for replica molding in poly(dimethylsiloxane) (PDMS). Specifically, liquid PDMS pre-polymer (Sylgard-184; Dow Corning) was mixed with curing agent, de-gassed, poured over the wafer, and cured to generate a negative cast. This process was repeated using the negative cast as a template to generate the PDMS surface containing square pyramidal micro-wells. For branching network and concentric circle substrates, patterns were first created in Inkscape and exported to Gcode. A 60-degree digitally-automated computer numerical control (CNC) mill was used to mill the pattern in high temperature epoxy followed by manual cleaning of the swarf with a syringe needle under a dissecting microscope. This master was then cleaned with 70% ethanol and cast in PDMS to create a patterning substrate.

Cell Isolation, Culture, and Labeling

Rat hepatocytes were isolated from 2-3 month old adult female Lewis rats (Charles River) by collagenase perfusion through the portal vein using methods described previously (March, S., et al. *Hepatology* 50, 920-928 (2009); Dunn, J. C., et al. *Biotechnol Prog* 7, 237-245 (1991) and Seglen, P. O. *Methods Cell Biol* 13, 29-83 (1976)). Briefly, animals were anesthetized with isoflorane and the portal vein was exposed and cannulated. The liver was perfused with buffers and then removed and digested with collagenase. The digest was purified using Percoll centrifugation. Hepatocyte viability was typically 85-95% based on trypan-blue exclusion assay. Hepatocytes were cultured in "hepatocyte media" containing DMEM with high glucose (Cellgro), 10% (v/v) fetal bovine serum (Gibco), 0.5 U/ml insulin (Lilly), 7 ng/ml glucagons (Bedford Laboratories), 7.5 µg/ml hydrocortisone (Sigma), and 1% penicillin-streptomycin (Invitrogen). J2-3T3 fibroblasts were cultured in DMEM with high glucose, 10% bovine serum, and 1% penicillin-streptomycin. Primary adult human hepatocytes were from a one year old female donor (Cryopreserved, Lot Hu8085, CellzDirect) and were cultured in high glucose DMEM (Cellgro) containing 10% fetal bovine serum (FBS; Gibco), 1% (vol/vol) ITS supplement (insulin, human transferring, and selenous acid; BD Biosciences), 0.49 pg/ml glucagon, 0.08 ng/ml dexamethasone, 0.018 M HEPES, and 1% (vol/vol) penicillin-streptomycin (pen-strep; Invitrogen). Liver endothelial cell line TMNK-1 were cultured in DMEM with high glucose, 10% FBS, and 1% penicillin-streptomycin, and used until passage 19. J2-3T3 fibroblasts were cultured in DMEM with high glucose, 10% bovine serum, and 1% pen-strep. Normal human dermal fibroblasts were cultured in DMEM with 10% FBS and 1% pen-strep. OVCAR-8 and HeLa cells were cultured in RPMI containing 10% FBS and 1% pen-strep. C2C12 skeletal myoblasts were cultured in DMEM with 20% FBS and 1% pen-strep. Cells were used between passages 7 and 19. Undifferentiated iPS were cultured and differentiated into iPS-hepatocyte-like cells via sequential addition of Activin A, bone morphogenic protein 4, basic FGF, HGF, and oncostatin M, as described previously (Schwartz, R. E., et al. *Proc Natl Acad Sci USA* 109, 2544-2548 (2012) and Si-Tayeb, K., et al. *Hepatology* 51, 297-305 (2010)). iPS-Heps were removed from culture after 15-17 days of differentiation. mCherry and GFP J2 fibroblasts were generated by ViroMag R/L (Oz Biosciences) mediated transduction of lentivirus containing mCherry or GFP under control of the EF1alpha promoter (Promega). Transduced mCherry or GFP J2s were subsequently selected by puromycin followed by fluorescence-activated cell sorting.

Hydrogel Materials

For agarose gels, ultra-pure low-melting point agarose was dissolved (Invitrogen) in DMEM (2% w/v). Liquid agarose solution was kept in a water bath at 37° C. until time of cell encapsulation and polymerization, at which point it was pipetted over patterned cells in the intaglio substrate and cooled at 4° C. to initiate gelation. Fibrin hydrogels were prepared by adding human thrombin (Sigma; 1.25 U/ml final concentration) to bovine fibrinogen (Sigma; 20 mg/ml final concentration) at the time of polymerization or by suspending cells in fibrinogen at the appropriate concentration, centrifuging into the secondary relief mold, and polymerizing via the addition of thrombin. For PEG hydrogels, cells were suspended in PEG pre-polymer solution, centrifuged into the secondary relief PEG material template, and then exposed to UV light from a spot curing system with collimating lens (320-390 nm, 90 mW/cm$^2$, 30 seconds, EXFO lite). PEG pre-polymer solution was composed of PEG-diacrylate (20 kDa at 10% (w/v); Laysan Bio) and 0.1% (w/v) Irgacure 2959 (Ciba).

Fabrication of Micro-patterned Engineered Tissues

For intaglio-relief molding (InVERT molding), the first cell population was either centrifuged or gravity settled (for hydrogels >1.5 cm or >10 cm in diameter) into the recessed features of the intaglio patterning substrate. A silicon gasket defining the XYZ dimensions of the resultant hydrogel was placed over the cells arrayed in the patterning substrate. For 'pre-incubation' (or 'pre-aggregation') based-encapsulation, cells were incubated overnight. The following day, the hydrogel material was carefully pipetted over the cells in the patterning substrate and polymerized. For 'immediate trapping', cells were spun into the patterning substrate directly in pre-polymer solution and then trapped in place by polymerization. Molded 3D hydrogels containing the first patterned cell type were then removed from the intaglio patterning substrate and inverted, exposing 'relief' features in the molded hydrogel. The inverted relief gel was placed into a second gasket system, and a second cell population in pre-polymer solution was centrifuged into the 'relief' pattern. Polymerization was triggered to entrap cells, resulting in the formation of a single hydrogel containing two distinct and micro-organized cellular compartments. Patterned hydrogels were then removed from the gasket and cultured in hepatocyte media.

For studies of hepatocyte and J2 fibroblast microorganization, 10-500 hepatocytes per microwell and corresponding J2 fibroblasts at ratios 1:1 or 1:2 were centrifuged into microwell templates (microwell side wall dimensions 400 µm). The following day, resultant aggregates were encapsulated in either agarose (FIG. 1) or fibrin (Supplemental Fig X) hydrogels. For studies of multi-compartmental organization, 100 hepatocytes and 25 J2 fibroblasts were patterned per microwell, incubated overnight, and then encapsulated in fibrin. Liver endothelial cells were then patterned using intaglio-relief molding in either "aggregate" (juxtaposed) or "lattice" (paracrine) conformations at a final concentration of two endothelial cells per hepatocyte. For multi-compartmental studies with iPS-Heps and stromal cells only, 100 iPS-Heps were patterned per well and J2 fibroblasts were patterned in various conformations at a ratio of 1:1 iPS-Hep: J2 Fibroblast. For studies in which intercompartmental distance was varied, 100 J2 fibroblasts expressing GFP were patterned in microwells with sidewall dimensions of 400 or 800 µm. Liver endothelial cells were then patterned using InVERT molding, and hydrogels were imaged using live imaging methods described below. For hydrogels of 14-15 cm diameter, J2 fibroblasts were fixed and stained with hematoxylin prior to encapsulation for macroscopic visualization. 800 fibroblasts per well were gravity settled into a 14-15 cm diameter patterning substrate containing microwells with side wall dimensions of 800 µm. Cells were encapsulated in fibrin gel and imaged with a Nikon digital SLR camera.

Microscopy and Automated Image Scanning

Imaging of hydrogels containing live cells stained with calcein, AM or calcein red-orange, AM (Invitrogen) was performed on a Nikon Eclipse TE200 or Olympus FV1000 Multiphoton Laser Scanning Confocal Microscope. For epifluorescence images, image viewing and analysis was performed in ImageJ (NIH) and Photoshop (Adobe). For multiphoton images, Z dimension between each slice was 2 µm. Images were stacked and merged for XYZ extended focus images, XZ sections, and movies using Volocity 3D Image Analysis software (PerkinElmer).

Automated image scanning of hydrogels containing microorganized cells was performed using a Nikon Eclipse Ti microscope equipped with an automated stage-scanning system. For studies determining patterning efficiency, hydrogels of 1.5 cm diameter containing micro-patterned cells were scanned and analyzed. Serial 4× magnification images were obtained and stitched automatically using NIS Elements software (Nikon; version 3.2). Image analysis and aggregate size quantification was performed using NIS Elements software.

Immunohistochemistry

For immunostaining of cellular aggregates, aggregates were collected from microwells, fixed in methanol and 10% acetic acid and gently pelleted in eppendorf tubes. Aggregates were resuspended in molten histogel (Thermo Scientific), repelleted, and placed on ice for histogel solidification. Histogel pellets were processed, embedded, and sectioned for immunohistochemistry. Sections were stained with a primary antibody against pan-cytokeratin (1:800, Sigma) followed by secondary Alexa 488-conjugated goat-anti-mouse antibody (Jackson ImmunoResearch). Images were obtained using a Nikon Eclipse TE200 microscope.

Biochemical Assays to Assess Hepatocyte Function

Rat albumin in sampled media was quantified by enzyme-linked immunosorbant assay using a sheep anti-rat albumin antibody and rat albumin ELISA kit (Bethyl labs). Urea in media samples was quantified by acid-catalyzed condensation of urea with diacetylmonoxime to give a colored-product that was measured spectophotometrically at 520 nm (Urea Nitrogen kit; StanBio Labs).

In vivo Implantation and Assessment of Engineered Tissues

All animal procedures were approved by The Committee for Animal Care in the Department of Comparative Medicine at Massachusetts Institute of Technology. Taconic NCr nude mice were anesthetized using isofluorane, and engineered tissues were placed into the intraperitoneal space via a 1 cm incision. The incision was closed aseptically, and animal recovery from surgery was monitored. Animals were administered 0.1 mg/ml buprenorphine every 12 hours for three days following surgical procedures.

To enable noninvasive imaging of hepatic function and survival of engineered tissues, hepatocytes were transduced in suspension culture immediately after isolation with a lentiviral vector expressing firefly luciferase under the human albumin promoter prior to engineered tissue fabrication. Mice were injected intraperitoneally with 250 μL of 15 mg/mL D-Luciferin (Caliper Life Sciences) and imaged using the IVIS Spectrum (Xenogen) system and Living Image software (Caliper Life Sciences).

Statistical Analysis

Experiments were independently repeated three times. All data in graphs are expressed as the mean±standard error. For normally distributes data, statistical significance was determined using one-way ANOVA followed by Tukey's post hoc test for group comparisons. Otherwise non-parametric Mann Whitney (for two-way comparisons) or the Kruskal-Wallace test followed by Dunn's Multiple Comparison (for group comparisons) was used. Alpha was set to 0.05 for all comparisons.

We claim:

1. A method of making a three-dimensional, multiple cell type tissue construct, comprising
    introducing a first population of cells into recessed features of a patterned cell capture substrate;
    encapsulating said first cell population in a first polymerizable biomaterial;
    polymerizing said first polymerizable biomaterial;
    removing and inverting said encapsulated first cell population thereby exposing an inverse pattern of the recessed features containing the first cell population in the first polymerizable biomaterial;
    contacting the inverse pattern of the recessed features comprising the, first cell population with a second population of cells in a second polymerizable biomaterial;
    encapsulating said second population in said second polymerizable biomaterial; and
    polymerizing said second polymerizable biomaterial,
    such that the three-dimensional, multiple cell type tissue construct is made.

2. The method of claim 1, wherein said first population of cells is incubated under conditions sufficient for formation of cell-cell junctions between cells in said features of said patterned cell capture substrate prior to encapsulating said first cell population in said first polymerizable biomaterial.

3. The method of claim 1, wherein the patterned cell capture substrate consists of polydimethyl siloxane (PDMS) comprising micro-scale features.

4. The method of claim 1, wherein the first population of cells is introduced into the features of the patterned cell capture substrate in a media or pre-polymer solution.

5. The method of claim 1, wherein said first population of cells is incubated for a period of about 6 to about 24 hours, to permit formation of cell-cell junctions between said cells.

6. The method of claim 1, wherein said first and/or second polymerizable biomaterial is a hydrogel material.

7. The method of claim 6, wherein the hydrogel material is agarose, fibrin, or polyethylene hydrogel.

8. The method of claim 7, wherein the hydrogel material is photopolymerized polyethylene glycol (PEG) hydrogel.

9. The method of claim 1, wherein the first or second cell population, or both the first and second cell populations comprise parenchymal cells.

10. The method of claim 1, wherein the first or second cell population, or both the first and second cell populations comprise non-parenchymal cells.

11. The method of claim 1, wherein the first or second cell population, or both the first and second cell populations comprise a combination of parenchymal and non-parenchymal cells.

12. The method of claim 9, wherein the parenchymal cells are human parenchymal cells.

13. The method of claim 5, wherein the hydrogel is derivatized with one or more cell-adhesive peptides, or comprises one or more soluble factors supporting cell growth and/or differentiation.

14. The method of claim 1, wherein the first or second cell populations, or both the first and second cell populations are encapsulated at a concentration of from about $8 \times 10^6$ cells/ml to about $24 \times 10^6$ cells/ml.

15. The method of claim 1, wherein the polymerizable biomaterial is biodegradable.

16. The method of claim 1, wherein one or more of the populations of cells is engineered to express a reporter protein.

17. The method of claim 1, wherein said first population of cells is incubated for a period of about 8 to about 16 hours to permit formation of cell-cell junctions between said cells.

18. The method of claim 1, wherein said first population of cells is incubated for a period of about 12 hours to permit formation of cell-cell junctions between said cells.

* * * * *

UNITED STATES PATENT AND TRADEMARK OFFICE
CERTIFICATE OF CORRECTION

| | |
|---|---|
| PATENT NO. | : 10,072,257 B2 |
| APPLICATION NO. | : 14/381866 |
| DATED | : September 11, 2018 |
| INVENTOR(S) | : Bhatia et al. |

Page 1 of 1

It is certified that error appears in the above-identified patent and that said Letters Patent is hereby corrected as shown below:

In the Specification

In Column 1, Lines 16-19, delete:
"This invention was made with government support under grant nos. EB008396 and DK56966 awarded by the National Institutes of Health (NIH). The government has certain rights in the invention."

And insert:
-- This invention was made with government support under EB008396 and DK056966 awarded by the National Institutes of Health. The government has certain rights in the invention. --

Signed and Sealed this
Ninth Day of December, 2025

John A. Squires
*Director of the United States Patent and Trademark Office*